United States Patent [19]
Thorwart et al.

[11] Patent Number: 6,159,995
[45] Date of Patent: Dec. 12, 2000

[54] SUBSTITUTED DIAMINOCARBOXYLIC ACIDS

[75] Inventors: Werner Thorwart, Hochheim; Wilfried Schwab, Wiesbaden; Manfred Schudok, Eppstein/Ts; Burkhard Haase, Hofheim; Bernhard Neises, Offenburg; Günter Billen, Niedernhausen, all of Germany

[73] Assignee: Aventis Pharma Deutschland GmbH, Frankfurt am Main, Germany

[21] Appl. No.: 09/074,587

[22] Filed: May 8, 1998

[30] Foreign Application Priority Data

May 9, 1997 [DE] Germany .............. 197 19 585
May 12, 1997 [DE] Germany .............. 197 19 428

[51] Int. Cl.[7] ............ A61K 31/55; A61K 31/54; A61K 31/535; A61K 31/495; A61K 31/505; A61K 31/425; A61K 31/42; A61K 31/415; A61K 31/40; C07D 513/00; C07D 277/62; C07D 277/28; C07D 249/12; C07D 249/08; C07D 235/04; C07D 403/02; C07D 233/61; C07D 209/02; C07D 209/36; C07D 207/40; C07D 207/30; C07D 207/18; C07D 243/00; C07D 417/00; A61P 19/00

[52] U.S. Cl. ............ 514/365; 514/210; 514/211; 514/212; 514/218; 514/226.8; 514/227.2; 514/227.8; 514/228.2; 514/228.5; 514/233.2; 514/234.5; 514/235.2; 514/235.8; 514/236.2; 514/237.2; 514/253; 514/255; 514/256; 514/274; 514/321; 514/323; 514/326; 514/338; 514/339; 514/341; 514/343; 514/367; 514/368; 514/372; 514/374; 514/376; 514/378; 514/380; 514/383; 514/384; 514/385; 514/389; 514/394; 514/397; 514/399; 514/406; 514/414; 514/416; 514/417; 514/418; 514/419; 514/422; 514/424; 514/425; 514/427; 514/428; 540/544; 540/553; 540/575; 540/602; 540/603; 544/55; 544/60; 544/61; 544/62; 544/96; 544/133; 544/139; 544/141; 544/142; 544/143; 544/144; 544/238; 544/295; 544/296; 544/310; 544/312; 544/314; 544/333; 544/357; 544/368; 544/370; 544/371; 544/372; 544/373; 546/193; 546/194; 546/197; 546/198; 546/199; 546/200; 546/201; 546/208; 546/210; 546/226; 546/232; 546/270.1; 546/273.4; 546/274.4; 546/274.7; 546/275.1; 546/276.4; 546/277.1; 546/277.7; 546/278.4; 548/126; 548/154; 548/159; 548/179; 548/180; 548/181; 548/186; 548/205; 548/217; 548/225; 548/228; 548/229; 548/235; 548/243; 548/247; 548/255; 548/263.2; 548/263.6; 548/265.8; 548/266.6; 548/304.7; 548/305.1; 548/305.4; 548/306.1; 548/312.1; 548/312.4; 548/312.7; 548/313.1; 548/314.7; 548/315.1; 548/315.4; 548/319.1; 548/340.1; 548/364.1; 548/364.7; 548/365.7; 548/455; 548/465; 548/485; 548/486; 548/494; 548/518; 548/525; 548/527; 548/547; 548/550; 548/561; 548/565; 548/569

[58] Field of Search ............ 544/60, 61, 62, 544/133, 139, 141, 142, 143, 144, 368, 370, 372, 373; 546/193, 194, 197, 198, 199, 200, 201, 208, 210, 226, 232, 270.1, 273.4, 274.4, 274.7, 275.1, 276.4, 277.1, 277.7, 278.4; 548/126, 154, 159, 179, 180, 181, 186, 205, 217, 225, 228, 229, 235, 243, 247, 255, 263.2, 263.6, 265.8, 266.6, 304.7, 305.1, 305.4, 306.1, 312.1, 312.4, 312.7, 313.7, 314.7, 315.1, 315.4, 319.1, 340.1, 364.1, 364.7, 365.7, 455, 465, 485, 486, 494, 518, 525, 527, 547, 550, 561, 565, 569; 514/227.8, 228.2, 228.5, 233.2, 234.5, 235.2, 235.8, 236.2, 237.2, 253, 255, 321, 323, 326, 338, 339, 341, 343, 365, 367, 368, 374, 376, 378, 380, 383, 384, 385, 389, 394, 397, 399, 406, 414, 416, 417, 418, 419, 422, 424, 425, 427, 428

[56] References Cited

FOREIGN PATENT DOCUMENTS

| | | |
|---|---|---|
| 0 305 947 B1 | 3/1989 | European Pat. Off. . |
| 0 468 231 B1 | 1/1992 | European Pat. Off. . |
| 0 606 046 B1 | 7/1994 | European Pat. Off. . |
| 0 757 037 A2 | 2/1997 | European Pat. Off. . |

(List continued on next page.)

OTHER PUBLICATIONS

Borkakoti, N., Matrix Metalloproteases: Variations on a Theme, Progress in Biophysics & Molecular Biology, vol. 70, pp. 73–94, 1998.

Yu et al., Matrix Metalloproteinases: Novel Targets for Directed Cancer Therapy, Drugs & Aging, vol. 11, No. 3, pp. 229–244, Sep. 1997.

HCAPLUS printout of WO 97/45402, Dec. 1997.

(List continued on next page.)

Primary Examiner—Richard L. Raymond
Assistant Examiner—Brenda Coleman
Attorney, Agent, or Firm—Finnegan, Henderson, Farabow, Garrett and Dunner, L.L.P.

[57] ABSTRACT

Compounds of formula (I)

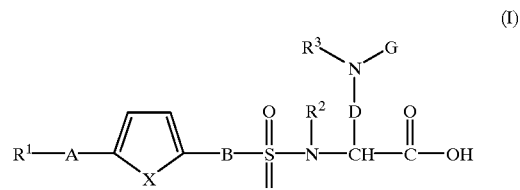

are suitable for the production of pharmaceuticals for the prophylaxis and therapy of disorders in the course of which an increased activity of matrix-degrading metalloproteinases is involved.

13 Claims, No Drawings

FOREIGN PATENT DOCUMENTS

| | | |
|---|---|---|
| WO 95/35276 | 12/1995 | WIPO . |
| WO 96/00214 | 1/1996 | WIPO . |
| WO 96/27583 | 9/1996 | WIPO . |
| WO 96/33172 | 10/1996 | WIPO . |
| WO 97/19068 | 5/1997 | WIPO . |

OTHER PUBLICATIONS

Bassin, Jatinder P. et al., "Chlorosulfonation of Some Polynuclear Heterocyclic Compounds," *Phosphorus, Sulfur, and Silicon,* vol. 72, pp. 157–170 (1992).

Fosang, Amanda J. et al., "Aggrecan Is Degraded by Matrix Metalloproteinases in Human Arthritis: Evidence that Matrix Metalloproteinase and Aggecanase Activities Can Be Independent," *J. Clin. Invest.,* vol. 98, No. 10, pp. 2292–2299 (Nov. 1996).

Roemmele, Renee C. And Rapoport, Henry, "Removal of N–Arylsulfonyl Groups from Hydroxy α–Amino Acids," *J. Org. Chem.,* vol. 53, pp. 2367–2371 (1988).

Suter, C. M., "Studies in the Diphenyl Ether Series. II. Preparation and Structure of Some Sulfonic Acids and Related Derivatives," *J. Am. Chem. Soc.,* vol. 53, pp. 1112–1116 (1931).

Wang, Su–Sun, "p–Alkoxybenzyl Alcohol Resin and p–Alkoxybenzyloxycarbonylhydrazide Resin for Solid Phase Synthesis of Protected Peptide Fragments," *J. Am. Chem. Soc.,* vol. 95, No. 4, pp. 1328–133 (Feb. 21, 1973).

Ye, Qi–Zhuang et al., "Purification and Characterization of the Human Stromelysin Catalytic Domain Expressed in *Escherichia coli,*" *J. Biochemistry,* vol. 31, pp. 11231–11235 (1992).

SUBSTITUTED DIAMINOCARBOXYLIC ACIDS

The invention relates to novel substituted diaminocarboxylic acids, processes for their preparation and use thereof as pharmaceuticals for the treatment of connective tissue disorders.

Patent applications EP 0 606 046, WO 95/35276 and WO 96/27583 describe arylsulfonamidohydroxamic acids and their action as matrix metalloproteinase inhibitors. Specific arylsulfonamidocarboxylic acids are used as intermediates for the preparation of thrombin inhibitors (EP 0 468 231) and aldose reductase inhibitors (EP 0 305 947). Patent application EP 0 757 037 also describes the action of sulfonylaminocarboxylic acid derivatives as metalloproteinase inhibitors.

The arylsulfonyl group has furthermore proven useful as an effective protective group of the amino function of α-aminocarboxylic acids (R. Roemmele, H. Rapoport, *J. Org. Chem.* 53 (1988) 2367–2371).

In the attempt to find active compounds for the treatment of connective tissue disorders, it has now been found that the diaminocarboxylic acids according to the invention are strong inhibitors of matrix metalloproteinases. Particular value is placed here on the inhibition of stromelysin (matrix metalloproteinase 3) and neutrophil collagenase (MMP-8), since both enzymes are substantially involved, as important constituents of the cartilaginous tissue, in particular in the degradation of the proteoglycans (A. J. Fosang et al., *J. Clin. Invest.* 98 (1996) 2292–2299).

The invention therefore relates to compounds of formula (I)

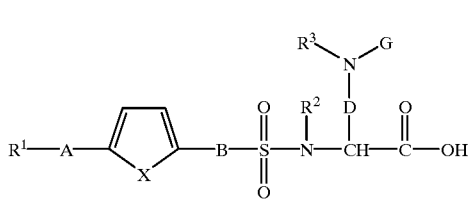

or a stereoisomeric form of the compound of formula (I), or a physiologically tolerable salt of the compound or stereoisomeric form of the compound of formula (I), where $R^1$ is
1. phenyl,
2. phenyl, which is mono- or disubstituted by
    2.1. ($C_1$–$C_7$)-alkyl, which is linear, cyclic, or branched,
    2.2. —OH,
    2.3. ($C_1$–$C_6$)-alkyl-C(O)—O—,
    2.4. ($C_1$–$C_6$)-alkyl-O—,
    2.5. ($C_1$–$C_6$)-alkyl-O—($C_1$–$C_4$)-alkyl-O—,
    2.6. halogen,
    2.7. —$CF_3$,
    2.8. —CN,
    2.9. —$NO_2$,
    2.10. HO—C(O)—,
    2.11. ($C_1$–$C_6$)-alkyl-O—C(O)—,
    2.12. methylenedioxo,
    2.13. $R^4$—($R^5$)N—C(O)—, or
    2.14. $R^4$—($R^5$)N—, or
3. a heteroaromatic ring structure as defined under 3.1. to 3.16., which is unsubstituted, or substituted by the radicals as defined under 2.1. to 2.14.,
    3.1. pyrrole,
    3.2. pyrazole,
    3.3. imidazole,
    3.4. triazole,
    3.5. thiophene,
    3.6. thiazole,
    3.7. oxazole,
    3.8. isoxazole,
    3.9. pyridine,
    3.10. pyrimidine,
    3.11. indole,
    3.12 benzothiophene,
    3.13. benzimidazole,
    3.14. benzoxazole,
    3.15. benzothiazole, or
    3.16. benzotriazole;

$R^2$, $R^4$ and $R^5$ are identical or different and each independently are
1. a hydrogen atom,
2. ($C_1$–$C_6$)-alkyl-,
3. HO—C(O)—($C_1$–$C_6$)-alkyl-,
4. phenyl-($CH_2$)$_o$—, in which phenyl is unsubstituted, mono- or disubstituted by the radicals as defined under 2.1. to 2.14., and o is the integer zero, 1, or 2,
5. picolyl, or
6. $R^4$ and $R^5$ together with the ring amino group form a 4- to 7-membered ring, in which one of the carbonyl atoms is optionally replaced by —O—, —S—, or —NH—;

$R^3$ and G are identical or different and each independently are
1. a hydrogen atom,
2. ($C_1$–$C_6$)-alkyl-, in which alkyl is linear, branched, or cyclic,
3. ($C_2$–$C_6$)-alkenyl-,
4. phenyl-($CH_2$)$_m$—, in which phenyl is unsubstituted, mono- or disubstituted by the radicals as defined under 2.1. to 2.14., and m is the integer zero, 1, 2, or 3,
5. heteroaryl-($CH_2$)$_m$—, in which heteroaryl is as defined under 3.1. to 3.16., is unsubstituted, or substituted by the radicals as defined under 2.1. to 2.14., and m is the integer zero, 1, 2, or 3,
6. $R^6$—C(O)—, in which
    $R^6$ is
    6.1. ($C_1$–$C_6$)-alkyl-, in which alkyl is unsubstituted, or substituted by the radicals as defined under 2.1. to 2.14., or by ($C_3$–$C_6$)-cycloalkyl,
    6.2. ($C_3$–$C_6$)-cycloalkyl, in which cycloalkyl is unsubstituted, or substituted by the radicals as defined under 2.1. to 2.14.,
    6.3. ($C_2$–$C_6$)-alkenyl-, in which alkenyl is unsubstituted, or mono-, di-, or trisubstituted by
        6.3.1. phenyl, in which phenyl is unsubstituted, or mono-, di-, or trisubstituted by the radicals as defined under 2.1. to 2.14.,
        6.3.2. heteroaryl-, in which heteroaryl is as defined under 3.1. to 3.16., and is unsubstituted, or mono-, di- or trisubstituted by the radicals as defined under 2.1. to 2.14., or
        6.3.3. the radicals as defined under 2.1. to 2.14.,
    6.4. phenyl-($CH_2$)$_m$—, in which phenyl is unsubstituted, or mono-, di- or trisubstituted by the radicals as defined under 2.1. to 2.14.,—O—$CF_3$, —$SO_2$—$NH_2$, —NH—C(O)—$CF_3$, or by benzyl, a hydrogen atom of the —($CH_2$)— radical is optionally substituted by the radical —COOH, and m is the integer zero, 1, 2, or 3, 6.5. naphthyl, 6.6. adamantyl, or 6.7. heteroaryl-$(CH_2)_m$—, in which heteroaryl is as defined under 3.1. to 3.16., is unsubstituted, or substituted by the radicals as defined under 2.1. to 2.14., and m is the integer zero, 1, 2, or 3, 7. $R^6$—O—C(O)—, in which $R^6$ is as defined above, 8. $R^6$—CH(NH$_2$)—C(O)—, in which $R^6$ is as defined above, 9. $R^8$—N($R^7$)—C(O)—, in which
$R^8$ is
9.1. a hydrogen atom
9.2. ($C_1$–$C_6$)-alkyl-,
9.3. phenyl-$(CH_2)_m$, in which phenyl is unsubstituted, or mono- or disubstituted by the radicals as defined under 2.1. to 2.14., and m is the integer zero, 1, 2, or 3, or
9.4. heteroaryl-$(CH_2)$m, in which heteroaryl is as defined under 3.1. to 3.16., is unsubstituted, or is substituted by the radicals as defined under 2.1. to 2.14., and m is the integer zero, 1, 2, or 3, and in which $R^7$ is a hydrogen atom, or ($C_1$–$C_6$)-alkyl, or in which $R^7$ and $R^8$ are bonded to a nitrogen atom to form a 4- to 7-membered ring and the ring is unsubstituted, or a carbon atom in the ring is replaced by —O—, —S—, or —NH—, 10. $R^6$—SO$_2$—, in which $R^6$ is as defined above, 11. $R^6$—SO$_2$—N($R^7$)—C(O)—, in which $R^6$ and $R^7$ are as defined above, 12. $R^6$—NH—C(=N$R^7$)—, in which $R^6$ and $R^7$ are as defined above, or
12.1. ($C_1$–$C_6$)-alkyl-C(O)—,
12.2. —NO$_2$, or
12.3. —SO$_2$—$(CH_2)_q$-phenyl, in which phenyl is unsubstituted, or mono- or disubstituted by the radicals as defined under 2.1. to 2.14., and q is the integer zero, 1, 2, or 3, in which m is the integer zero, 1, 2, or 3, and W is a nitrogen, oxygen, or sulfur atom; or $R^3$ and G are bonded to a nitrogen atom to form a ring of subformulae (IIa) to (IIp), -continued

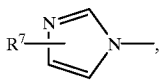 (IIj)

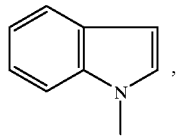 (IIk)

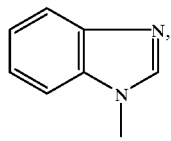 (IIl)

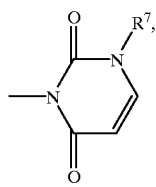 (IIm)

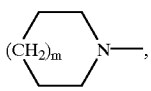 (IIn)

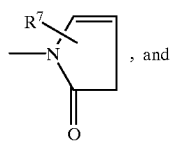 (IIo), and

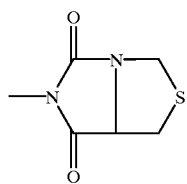 (IIp)

where r is the integer 1 or 2, $R^{10}$ is a radical as defined under 2.1. to 2.14., and $R^7$ and m are as defined above, and in subformula (IIg) a carbon atom in the ring is optionally replaced by oxygen, sulfur, $SO_2$, or a nitrogen atom which is unsubstituted or substituted by $R^2$;

A is
  a) a covalent bond,
  b) —O—,
  c) —CH=CH—, or
  d) —C≡C—;

B is
  a) —$(CH_2)_m$—, in which m is as defined above,
  b) —O—$(CH_2)_q$, in which q is the integer 1, 2, 3, 4, or 5, or
  c) —CH=CH—;

D is
  —$(CH_2)_m$— in which m is the integer 1, 2, 3, 4, 5, or 6, and one of the chain carbon atoms is optionally replaced by an optionally substituted —NH—, —O—, or —S—atom; and X is
  —CH=CH—, an oxygen atom, or a sulfur atom.

A currently preferred compound of formula (I) is where
$R^1$ is
  1. phenyl, or
  2. phenyl, which is monosubstituted by
    1. halogen, in particular chlorine or fluorine, or
    2. $R^4$—$(R^5)N$—, where $R^4$ and $R^5$ are identical or different and each independently are
      2.1. $(C_1-C_3)$-alkyl, or
      2.2. $R^4$ and $R^5$ together with the ring amino group form a 5- or 6-membered ring, where one of the carbon atoms is optionally replaced by —O—or —NH—;

$R^2$ is a hydrogen atom;

G and $R^3$ are different, and where
  G is a hydrogen atom, or $(C_1-C_4)$-alkyl, and
  $R^3$ is
    1. phenyl-$(CH_2)_m$, in which phenyl is unsubstituted, mono- or disubstituted by the radicals as defined under 2.1. to 2.14., and m is the integer 1,
    2. heteroaryl-$(CH_2)_n$, in which heteroaryl is as defined under 3.10. and is unsubstituted, or substituted by the radicals as defined under 2.1. to 2.14., and n is zero,
    3. is $R^6$—C(O)—, in which
      $R^6$ is
        3.1. $(C_1-C_6)$-alkyl-, in which alkyl is linear, branched, or cyclic,
        3.2. phenyl-$(CH_2)_r$— in which phenyl is unsubstituted, or mono- or disubstituted by the radicals as defined under 2.1. to 2.14., a hydrogen atom of the —$(CH_2)$—radical is optionally replaced by the radical —COOH, and r is zero, 1, 2, or 3, or
        3.3. heteroaryl-$(CH_2)_o$-, in which heteroaryl is as defined under 3.1. to 3.15., and is unsubstituted, or substituted by the radicals as defined under 2.1. to 2.14., and o is zero, 1,2, or 3, or
    4. is $R^8$—N($R^7$)—C(O)—, in which
      $R^8$ and $R^7$ are bonded to a nitrogen atom to form a 5- or 6-membered ring, in which the ring is unsubstituted, or a ring carbon atom is replaced by an oxygen atom, or
  $R^3$ and G are bonded to a nitrogen atom to form a ring of subformula (IIg), in which r is 1;

A is a covalent bond;
B is $(CH_2)_p$—, in which p is zero;
D is —$(CH_2)_q$—, in which q is the integer 2, 3, or 4; and
X is—CH=CH—.

The expression "$R^4$ and $R^5$ together with the ring amino group form a 4- to 7-membered ring, in which one of the carbon atoms is replaced by —O—, —S—, or —NH—" is understood as meaning radicals which are derived, for example, from pyrrolidine, piperazine, morpholine, piperidine, or thiomorpholine. The term "halogen" is understood as meaning fluorine, chlorine, bromine, or iodine. The term "alkyl" or "alkenyl" is understood as meaning hydrocarbon radicals whose carbon chains are straight-chain or branched. Cyclic alkyl radicals are, for example, 3- to 6-membered monocyclic systems such as cyclopropyl, cyclobutyl, cyclopentyl, or cyclohexyl, which may or may not have substituent groups attached to the ring. The alkenyl radicals can furthermore also contain one or more double bonds.

The starting substances of the chemical reactions are known or one of ordinary skill in the art can easily derive and prepare such starting substances by methods known from the literature.

The invention furthermore relates to a process for the preparation of a compound of formula (I), or a stereoisomeric form of a compound of formula (I), or a physiologically tolerable salt of a compound or stereoisomeric form of a compound of formula (I), which comprises a) reacting a diaminocarboxylic acid of formula (III),

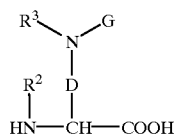
(III)

in which $R^2$, $R^3$, D, and G are as defined in formula (I), with a sulfonic acid derivative of formula (IV)

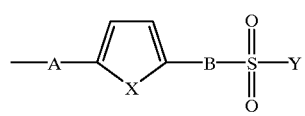
(IV)

in which $R^1$, A, and B are as defined in formula (I), and Y is a halogen atom, imidazolyl, or —$OR^9$, in which $R^9$ is a hydrogen atom, ($C_1$–$C_6$)-alkyl, phenyl, succinimidyl, benzotriazolyl, or benzyl, optionally substituted, in the presence of a base or if appropriate of a dehydrating agent, to give a compound of formula (V); or b) reacting a diaminocarboxylic acid ester of formula (V),

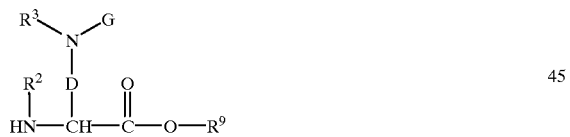
(V)

in which $R^2$, $R^3$, D, G, and $R^9$ are defined as above, with a sulfonic acid derivative of formula (IV) under the above defined conditions to give a compound of formula (VI)

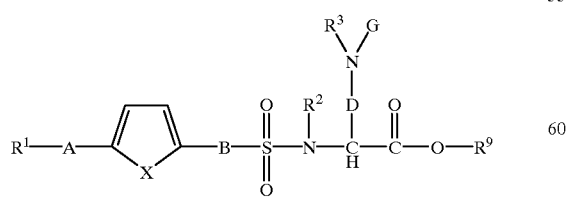
(VI)

and converting the compound of formula (VI) into a compound of formula (I) with removal of the radical $R^9$, preferably in the presence of a base or acid;

c) reacting the protected diaminocarboxylic acids of formula (VII);

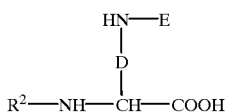
(VII)

in which $R^2$ and D are as defined above, and E is a protective group of the amino function, with a sulfonic acid derivative of formula (IV), to give a compound of formula (VIII)

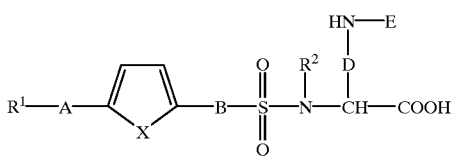
(VIII)

and then converting the compound of formula (VIII), by removal of the protective group E with the aid of suitable cleavage agents, into a compound of formula (I)

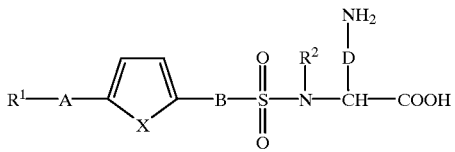
(I)

in which $R^1$, $R^2$, A, B, D, and X are as defined above, and $R^3$ and G are both hydrogen atoms, and reacting this compound of the formula (I) if appropriate with the aid of $R^3$—Y, in which $R^3$ and Y have the meanings defined above, in the presence of a base to give a compound of formula (I),

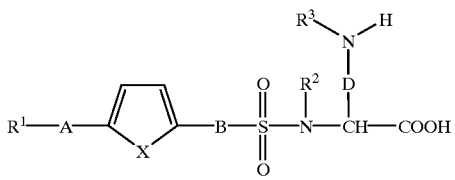
(I)

in which $R^1$, $R^2$, $R^3$, A, B, and X are as defined above, and G is a hydrogen atom; or d) as starting compounds, converting protected diamino acid esters of formula (IX),

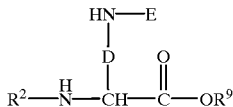
(IX)

in which $R^2$, $R^9$, D, and E are as defined above, in the same manner as described in process variant c), into the esters of formula (X),

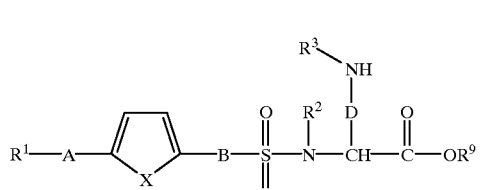
(X)

which are optionally converted into the corresponding compounds of formula (I) according to process variant b); or e) coupling a diaminocarboxylic acid of formula (XI),

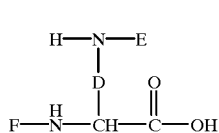
(XI)

in which D is defined as in formula (I), and E and F are N-amino protective groups which are different from one another, by its carboxyl group —C(=O)O— via an intermediate chain L to a polymeric resin depicted as PS, resulting in a compound of formula (XII)

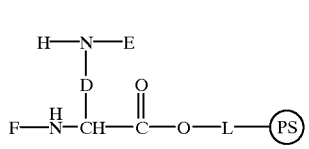
(XII)

which, after selective removal of the protective group F, is reacted with a sulfonic acid derivative of formula (IV)

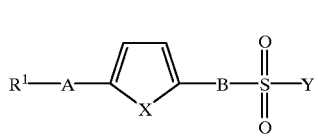
(IV)

where $R^1$, A, B, and Y are as defined above, in the presence of a base or, if appropriate, of a dehydrating agent, to give a compound of formula (XIII)

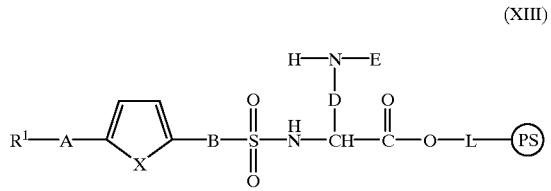
(XIII)

and reacting the compound of formula (XIII), after removal of the protective group E, with a carboxylic acid derivative of formula (XIV)

R—C(O)—Y (XIV)

in which $R^6$ and Y are as defined above, in the presence of a base or of a dehydrating agent, to give a compound of formula (XV)

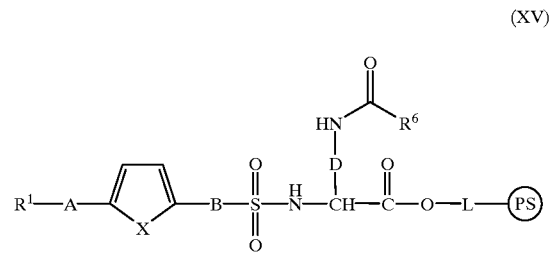
(XV)

and converting this, after removal from the support material, into a compound of formula (I),

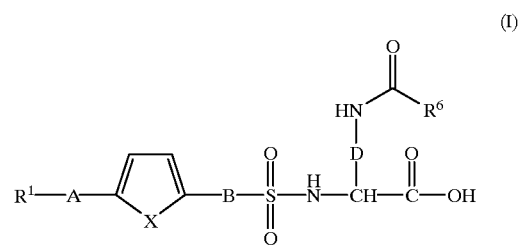
(I)

in which $R^1$, $R^6$, A, B, D, and X are defined as above.

Starting compounds of formula (III) employed in which $R^2$, $R^3$, and G are a hydrogen atom preferably included 2,3-diaminopropionic acid, 2,4-diaminobutyric acid, ornithine, lysine and homolysine. If $R^3$ and G, together with the amino function, are a guanidyl group, arginine is preferably used.

If, as in process variants c), d) and e), the amino functions of the starting compounds of formulae (VII), (IX) and (XI) are provided with a protective group E or F, this selective amino group derivatization is carried out according to methods such as are described in Houben-Weyl *Methoden der Org. Chemie* [Methods of Organic Chemistry], Volume 15/1 (1993).

Suitable protective groups E and F for this purpose are preferably the N-protective groups customarily used in peptide chemistry, for example protective groups of the urethane type, such as benzyloxycarbonyl (Z), t-butoxycarbonyl (Boc), 9-fluorenyl-methoxycarbonyl (Fmoc) and allyloxycarbonyl (Aloc), or of an acid amide type, in particular formyl, acetyl, or trifluoroacetyl, or of an alkyl type such as benzyl. The (trimethylsilyl) ethoxycarbonyl (Teoc) group has proven particularly suitable for this purpose (P. Kociénski,-*Protecting Groups*, Thieme Verlag, 1994). Many of the selectively derivatized compounds are also commercially available, so the preparation of the compounds of formula (I) according to the invention, as described in process variant c), comprises carrying out, after the introduction of the sulfonic acid ester into the α-amino group, the removal of the side-chain protective group E, which can optionally be followed by a multi-stage derivatization of the free amino group in the side chain. During this procedure, the carboxyl group can be present in free form or in the form of an ester with the radical —$OR^9$. In the case in which the radical —$OR^9$ is a straight-chain ($C_1$–$C_3$)-alkyl radical, this ester of formula (I) can also be employed in therapy in this form (as a prodrug). When $R^9$ is a tert-butyl radical, the ester cleavage is preferably carried out according to known methods using HCl in diethyl ether or trifluoroacetic acid in the last synthesis stage.

Starting materials for the preparation of the sulfonic acid derivatives of formula (IV) are preferably sulfonic acids or their salts of the formulae (XVIa)–(XVIg), for example:

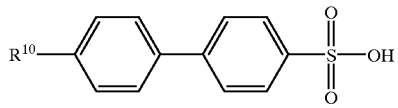
(XVIa)

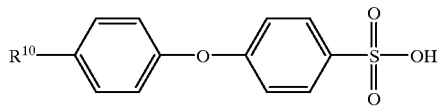
(XVIb)

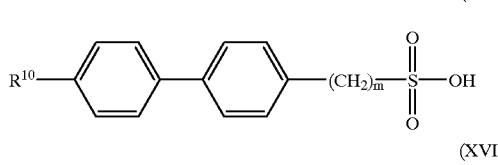
(XVIc)

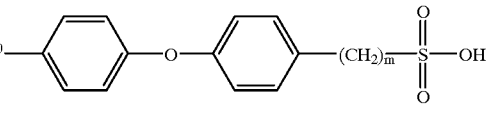
(XVId)

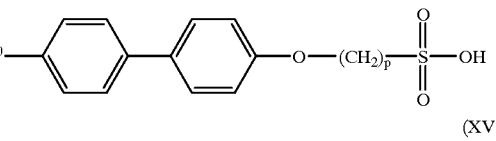
(XVIe)

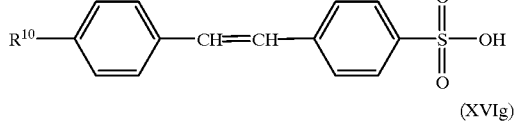
(XVIf)

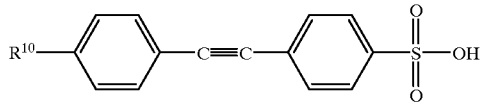
(XVIg)

where $R^{10}$ is a radical as defined under 2.1 to 2.14.

For the preparation of the arylsulfonic acids of formulae (XVIa) and (XVIb), use is preferably made of the sulfonation process using concentrated sulfuric acid described in Houben-Weyl *Methoden der Organischen Chemie* [Methods of Organic Chemistry], Volume 9 (1993), pp. 450–546, if appropriate in the presence of a catalyst, sulfur trioxide and its addition compounds or halosulfonic acids, such as chlorosulfonic acid. Particularly in the case of the diphenyl ether of formula (XVIb), the use of concentrated sulfuric acid and acetic anhydride as solvents (C. M. Suter, *J. Am. Chem. Soc.* 53 (1931) 1114), or the reaction with excess chlorosulfonic acid (J. P. Bassin, R. Cremlyn and F. Swinbourne; *Phosphorus, Sulfur and Silicon* 72 (1992) 157) has proven suitable. Sulfonic acids according to the formulae (XVIc), (XVId), or (XVIe) can be prepared in a known manner in which the corresponding arylalkyl halide is reacted with sulfites such as sodium sulfite or ammonium sulfite in aqueous or aqueous/alcholic solution. It is possible to accelerate the reaction in the presence of tetraorganoammonium salts such as tetrabutylammonium chloride.

The sulfonic acid derivatives according to formula (IV) are in particular the sulfonyl chlorides. For their preparation, the corresponding sulfonic acids, also in the form of their salts such as sodium, ammonium or pyridinium salts, are reacted in a known manner with phosphorus pentachloride or thionyl chloride without or in the presence of a solvent such as phosphorus oxytrichloride or of an inert solvent such as methylene chloride, cyclohexane or chloroform, in general at reaction temperatures from 20° C. up to the boiling point of the reaction medium used.

The reaction of the sulfonic acid derivatives of formula (IV) with the amino acids of formulae (III), (V), (VII) or (IX) according to process variant a), b), c) or d) proceeds advantageously in the manner of a Schotten-Baumann reaction. Suitable bases for this purpose are particularly alkali metal hydroxides such as sodium hydroxide, but also alkali metal acetates, hydrogencarbonates, carbonates and amines. The reaction takes place in water or in a water-miscible or immiscible solvent such as tetrahydrofuran (THF), acetone, dioxane or acetonitrile, the reaction temperature in general being kept at from –10° C. to 50° C. In the case in which the reaction is carried out in anhydrous medium, tetrahydrofuran or methylene chloride, acetonitrile or dioxane in the presence of a base, such as triethylamine, N-methylmorpholine, N-ethyl- or diisopropyl ethyl amine, is especially used, possibly in the presence of N,N-dimethylaminopyridine as the catalyst.

In another variant, the aminocarboxylic acids of the formulae (111), (V), (VII) or (IX) can first be converted into their silylated form with the aid of a silylating agent such as bis-trimethylsilyltrifluoroacetamide (BSTFA) and they can then be reacted with sulfonic acid derivatives to give compounds of formula (I).

The polymeric support designated by PS in formula (XII) is a crosslinked polystyrene resin having a linker designated L as an intermediate chain, known as a Wang resin (S. W. Wang, *J. Am. Chem. Soc.* (1973), 1328, p-benzyloxybenzyl alcohol polystyrene resin). Alternatively, other polymeric supports such as glass, cotton or cellulose having various intermediate chains L can be employed.

The intermediate chain designated by L is covalently bonded to the polymeric support and allows a reversible, ester-like bonding with the diamino acid of formula (XI), which during the further reaction remains stably bonded to the diaminocarboxylic acid, but under strong acidic reaction conditions (e.g., pure trifluoroacetic acid) releases the group located on the linker again.

The release of the desired compound of the formula (I) from the linker can be carried out in various places in the reaction sequence.

1) In the case of a compound of the formula (I) in which $R^3$ and G are hydrogen, the α-sulfonylamino-ω-carboxylic acid derivative, after removal of the protective group E, is liberated by treatment of the resin with trifluoroacetic acid.
2) If a compound of formula (I) in which $R^3$ is hydrogen and G is $R^6$—C(O)— is to be obtained, the release of the compound from the resin is carried out after simple acylation with $R^6$—C(O)—Y, as in 1).
3) For the case of a compound of formula (I) in which $R^3$ and G are $R^6$—C(O)—, the removal is only carried out after thorough diacylation with the aid of an acylating catalyst, e.g., dimethylaminopyridine, as in 1).
4) This procedure furthermore allows the radicals 2. to 13. defined in formula (I) for $R^3$ and G to be coupled at this position in the reaction sequence to the α-sulfonylamido-ω-aminocarboxylic acid bonded to the solid support using suitable reagents, e.g., alkyl halides, alkenyl halides, chloroformates, isocyanates, sulfonic acid derivatives, or cyclic anhydrides. After removal of the resulting compounds from the solid support, the corresponding substituted amines, urethanes, ureas, sulfonamides or amides, for example, are thus also obtained.

A. General procedure for the coupling of protected diaminocarboxylic acids of formula (XI) to the solid support according to procedure e): 2 g of Wang resin (Nova-Biochem; loading 0.5 mmol/g) are allowed to swell in 20 ml of dry dichlormethane for 30 min (50 ml PET syringe with a Teflon filter on the syringe bottom). After filtering the solvent, the syringe is filled with a solution of 3.5 mmol of the appropriate ω-Teoc-α-Fmoc diaminocarboxylic acid (prepared according to D. H. Rich et al., Synthesis 198, 346), 3.5 mmol of diisopropylcarbodiimide and 0.5 mmol of N,N-dimethylaminopyridine in approximately 10 ml of dry dichloromethane and shaken at room temperature (RT) for 16 hours (h).
After filtering off the reaction mixture, the resin is washed several times with dichloro-methane and dried and weighed to determine the yield.

B. Removal of the α-Fmoc protective group: The resin prepared as in A. is allowed to swell in the syringe in approximately 20 ml of dry dimethylformamide (DMF) and then, after filtering off the solvent, treated with 25% strength piperidine/DMF solution and shaken at RT for 45 minutes (min). The resulting mixture is filtered and the resin remaining in the syringe is washed several times with dry DMF. (The filtrate and all wash solutions can be stored to determine the Fmoc removal; for implementation see: *Solid Phase Peptide Synthesis—A Practical Approach*, E. Atherton and R. C. Sheppard, IRL Press at Oxford University Press 1989).

C. Sulfonation of the free cc-amino group: The contents of the syringe are then uniformly distributed into four smaller syringes provided with an inserted filter plate and treated with solutions of various sulfonic acid derivatives of formula (IV) (in each case 1 mmol) and diisopropylethylamine (in each case 1 mmol) in 3 ml of dry DMF and shaken at RT for 24 h. The reagent solution is then washed out and the resin is washed several times with DMF.

D. Removal of the Teoc protective group: The resin prepared as in step C. is treated with a molar N-tetrabutylammonium fluoride solution in DMF (in each case approximately 3 ml) and shaken at RT for 2 h. The reagent solutions are filtered and the remaining resin is washed several times with DMF. The syringe contents of each of the 4 individual syringes are then distributed, for example, into each of a further 3 prepared syringes. (In each case 1× 0.05 mmol and 2× 0.1 mmol).

E.1: Removal from the solid support: In each case approximately ⅓ of the contents of a syringe is washed with dichloromethane (approximately 10 ml) to remove the substance from the solid support, dried and shaken at RT for 1 h with approximately 1 ml of a solution of 95% trifluoroacetic acid, 2% $H_2O$, and 3% triisopropylsilane.
The filtered solution from the syringe is evaporated, and precipitated with diethyl ether. The solid residue is filtered for further purification and dried.

E.2: Acylation with carboxylic acid derivatives of the formula $R^6$—C(O)—Y: The other syringes are in each case filled with 1 molar solutions of acetic anhydride (1 equivalent based on liberated amine, or 3 equivalents for bis-acylations) and a corresponding amount of triethylamine in DMF and shaken at RT for 16 hours (completeness of the acylation can be checked, for example, by the Kaiser-Ninhydrin test (for implementation see: *Solid Phase Peptide Synthesis—A Practical Approach*, E. Atherton and R. C. Sheppard, JRL Press at Oxford University Press 1989).

E.3: Removal of the compounds of formula (XV) from the solid support: The resins prepared in E.2: are washed with dichloromethane as described in E.1:, dried and treated at RT for 1 h with trifluoroacetic acid/$H_2O$/triisopropylsilane 95/2/3. The solutions obtained are worked up as described in E.1:.

Physiologically tolerable salts are prepared from compounds of formula (I) capable of salt formation, including their stereoisomeric forms, in a manner known to those skilled in the art. With basic reagents, such as hydroxides, carbonates, hydrogencarbonates, alcoholates and also ammonia or organic bases (e.g. trimethyl- or triethylamine, ethanolamine or triethanolamine) or, alternatively, basic amino acids (e.g. lysine, ornithine or arginine) the carboxylic acids form stable alkali metal, alkaline earth metal or optionally substituted ammonium salts. If the compounds of formula (I) have basic groups, stable acid addition salts can also be prepared with strong acids. Those suitable for this purpose are both inorganic and organic acids such as hydrochloric, hydrobromic, sulfuric, phosphoric, methanesulfonic, benzenesulfonic, p-toluenesulfonic, 4-bromobenzenesulfonic, cyclohexylamidosulfonic, trifluoromethylsulfonic, acetic, oxalic, tartaric, succinic, or trifluoroacetic acid.

The invention also relates to pharmaceuticals comprising an efficacious content of at least one compound of formula (I), or an optionally stereoisomeric form of the compound of formula (I), or of a physiologically tolerable salt of the compound or of the stereoisomeric form of the compound of formula (I), together with a pharmaceutically suitable and physiologically tolerable excipient, additive or other active or inactive compounds and auxiliaries.

On account of the pharmacological properties, the compounds according to the invention are suitable for the prophylaxis and therapy of all those disorders in the course of which an increased activity of matrix-degrading metalloproteinases is involved. These include degenerative joint disorders such as osteoarthroses, spondyloses, chondrolysis after joint trauma or relatively long immobilization of the joint after meniscus or patella injuries or tears of the ligaments. Furthermore, these also include disorders of the connective tissue such as collagenoses, periodontal disorders, wound healing disorders and chronic disorders of the locomotory apparatus such a s inflammatory, immunologically or metabolically related acute and chronic arthritides, arthropathies, myalgias and disorders of the bone metabolism. The compounds of formula (I) are furthermore suitable for the treatment of ulceration, atherosclerosis and stenoses. The compounds of formula (I) are furthermore suitable for the treatment of inflammation, carcinomatous disorders, formation of tumor metastases, cachexia, anorexia and septic shock.

The pharmaceuticals according to the invention are in general administered orally or parenterally. Transmucosal (such as rectal) and transdermal administration are also possible.

The invention also relates to a process for the production of a pharmaceutical, which comprises bringing at least one compound of formula (I) into a suitable administration form using a pharmaceutically suitable an d physiologically tolerable excipient and, if appropriate, other suitable active compounds, additives or auxiliaries.

Suitable solid or pharmaceutical preparation forms are, for example, granules, powders, coated tablets, tablets, (micro)capsules, suppositories, syrups, juices, suspensions, emulsions, drops or injectable solutions and also preparations with protracted release of active compound, in whose preparation customary auxiliaries, such as excipients, disintegrants, binders, coating agents, swelling agents, glidants or lubricants, flavorings, sweeteners and solubiliizers are used. Frequently used auxiliaries which may be mentioned are magnesium carbonate, titanium dioxide, lactose, mannitol and other sugars, talc, lactoprotein, gelatin, starch, cellulose and its derivatives, animal and vegetable oils such as fish liver oil, sunflower, groundnut, or sesame oil, polyethylene glycol and solvents such as, for example, sterile water and mono- or polyhydric alcohols such as glycerol.

The pharmaceutical preparations are preferably prepared and administered in dose units, each unit as active constituent containing a specific dose of the compound of formula (I) according to the invention. In solid dose units such as tablets, capsules, coated tablets, or suppositories, this dose can be up to approximately 1000 mg, but the currently preferred dose is approximately 50 to 300 mg, and in injection solutions in ampoule form up to approximately 300 mg, but the currently preferred dose is approximately 10 to 100 mg.

For the treatment of an adult patient weighing approximately 70 kg, depending on the efficacy of the compounds according to formula (I), daily doses of approximately 20 mg to 1000 mg, preferably approximately 100 mg to 500 mg, are indicated. Under certain circumstances, however, higher or lower daily doses may be appropriate. The daily dose can be administered both by single administration in the form of an individual dose unit or else of several smaller dose units and by multiple administration of subdivided doses at specific intervals.

$^1$H-NMR spectra have been recorded on a 200 MHz apparatus from Varian, as a rule using tetramethylsilane (TMS) as an internal standard and at room temperature (RT). The solvents used are indicated in each case. As a rule, final products are determined by mass-spectroscopic methods (FAB-, ESI-MS). Temperature data are given in degrees Celsius, RT means room temperature (22–26° C.). Abbreviations used are either explained or correspond to the customary conventions unless specified otherwise.

EXAMPLE 1

(R)-(4-Chlorobiphenylsulfonyl)citrulline

Prepared according to process variant a): 1.7 g (9.7 mmol) of R-citrulline are dissolved in 19.4 ml of 0.5 N NaOH and, after addition of 40 ml of THF, slowly treated at 0° C. with a further 19.4 ml of the sodium hydroxide solution and at the same time 9.7 ml of a 1 molar solution of 4-chlorobiphenylsulfonyl chloride. After stirring at room temperature for 16 hours (h), the reaction mixture is concentrated on a rotary evaporator and treated with 20 ml of ethyl acetate. On acidification with 1 M HCl, a white precipitate is deposited, which is filtered off with suction and dried.

Yield: 2.26 g (54% of theory)
$^1$H-NMR (DMSO-$d_6$): 1.2–1.7 (2m, 4H); 2.9 (dd, 2H); 3.7 (dd, 1H); 5.4 (s, 2H); 5.9 (t, 1H); 7.5–7.9 (2 d, s, 8H); 8.2 (d, 1H)

EXAMPLE 2

R-(4-Chlorobiphenylsulfonyl)-Lys(Boc)-OH

Prepared according to process variant c): The reaction of 5.15g (21 mmol) of H-D-Lys(Boc)-OH to give (4-chlorobiphenyl-sulfonyl)-R-Lys(Boc)-OH is carried out as described in Example 1; the workup, however, is carried out by extraction with ethyl acetate and evaporation of the solvent under reduced pressure.

Yield: 9.3 g (89% of theory)
$^1$H-NMR (DMSO-$d_6$): 1.1–1.7 (m, 15H), 2.8 (dd,2H), 3.7 (m, 1H), 6.7 (t,1H), 7.6; 7.8 (2d, 4H), 7.9 (m,4H), 8.2 (d, 1H)

EXAMPLE 3:

R-(4-Chlorobiphenylsulfonyl)-Lys-OH 4.97g (10 mmol) of the compound from Example 2 are treated for 30 min at RT with 15 ml of 50% strength TFA in methylene chloride. Evaporation under reduced pressure affords the desired compound.

Yield: 3.73 g (94% of theory)
$^1$H-NMR (DMSO-$d_6$): 1.1–1.7 (m, 6H), 2.8 (dd,2H), 3.7 (m, 1H), 6.6 (m,2H), 7.6; 7.8 (2d, 4H), 7.9 (m,4H), 8.2 (d, 1H)

EXAMPLE 4

4-Chlorobiphenylsulfonyl-N-epsilon-(5-methylisoxazol-4-carbonyl)-Lys-OH 0.15 g (0.345 mmol) of the (4-chlorobiphenylsulfonyl) lysine from Example 3 is stirred at RT for 6 h with 50.1 mg (0.345 mmol) of 5-methylisoxazole-4-carbonyl chloride and 86.9 mg (1.035 mmol) of NaHCO$_3$ in 5 ml of acetonitrile. The solvent is then distilled off under reduced pressure, the residue is taken up in ethyl acetate and the solution is extracted several times by shaking under hydrochloric acid and also neutral conditions. After drying the organic phase and filtering off the drying agent, the solution is evaporated under reduced pressure.

Yield: 0.11 g (63% of theory)
$^1$H-NMR (DMSO-$d_6$): 1.1–1.7 (mm, 7H); 2.6 (2 s, 3H); 2.8; 3.1 (2 m, 2H); 3.7 (m, 1H); 7.6; 7.8 (2 d, 4H); 7.9 (m, 5H); 8.2 (d, 1H); 8.8 (2 s, 1H)

EXAMPLE 5

(4-Chlorobiphenylsulfonyl)-N-delta-(phenylsulfonylaminocarbonyl)-Orn-OH

Prepared according to process variant d):

5 a. Reaction of H-Orn(Z)-OtBu to give 4-chlorobiphenylsulfonyl-Orn(Z)-OtBu: 11.27 g (31.4 mmol) of H-Orn(Z)-OtBu-hydrochloride are reacted with 9.02 g (31.4 mmol) of 4-chlorobiphenylsulfonyl chloride and 10.7 ml (61.8 mmol) of diisopropylethylamine at 0° C. in 200 ml of THF. After 4 h, the batch is evaporated under reduced pressure and the residue is extracted, after taking it up in ethyl acetate, by shaking under hydrochloric acid, neutral and basic conditions (sodium carbonate solution). After drying the organic phase, the desired product is obtained after evaporation to dryness.

Yield: 16.7 g (93% of theory)
$^1$H-NMR (DMSO-$d_6$): 1.5 (s, 9H); 1.3–1.5 (m, 4H); 2.9 (m, 2H); 3.6 (m, 1H);
5.0 (s, 2H); 7,3 (m, 6H); 7,5; 7,7 (2d, 4H); 7,8 (s, 4H); 8,2 (d, 1H)

5 b. Removal of the benzyloxycarbonyl protective group (Z): 16.7 g (29 mmol) of the product from 5a is dissolved in methanol-ethyl acetate 1:1 and hydrogenated with 4 g of 10% Pd/C under a slight overpressure for 16 h. The catalyst is then filtered off and the residue is evaporated under reduced pressure.

Yield: 11.2 g(91% of theory)
$^1$H-NMR: The characteristic signals of the protective group are absent (5.0; 7.3).

5c. Reaction of 5b to give the phenylsulfonylurea derivative: 0.5 g (.14 mmol) of the compound described in 5 b is reacted with 0.23 ml of phenylsulfonyl isocyanate in dimethylacetamide at RT. After 16 h, the solvent is removed and the crystalline product precipitating from ethyl acetate is after treated with diethyl ether. Diethyl ether residues are removed under reduced pressure.

Yield: 0.53 g (75% of theory)

¹H-NMR (DMSO-d₆): 1.1 (s, 9H); 1.3–1.5 (m, 4H); 2.9 (m, 2H); 3.6 (m, 1H); 6.5 (t, 1H); 7.4–7.9 (mm, 14H); 8.2 (d, 1H); 10.6 (s, 1H)

5d. Removal of the protective group of Example 5c: 0.52 g of the abovementioned product 5 c is stirred a t RT for 45 min with 5 ml of TFA. TFA is removed under reduced pressure; the residue is coevaporated twice wth toluene, suspended in diethyl ether and separated off as a white crystalline solid as in Example 5.

Yield: 0.4 g (84% of theory)

¹H-NMR (DMSO-d6): 1.3–1.5 (m, 4H); 2.9 (m, 2H); 3.6 (m, 1H); 6.5 (t, 1H); 7.4–7.9 (mm, 14H); 8.2 (d, 1H); 10.6 (s, 1H)

EXAMPLE 6

2-(2R)-(4-Chlorobiphenylsulfonylamino)-5-phthalimidoyl-pentanoic acid 0.7 g (1.67 mmol) of 2-(2R)-(4-chlorobiphenylsulfonylamino)-5-amino-pentanoic acid hydrochloride, prepared according to process variant c) is heated to 150° C. for 1 hour with 0.358 g (2.42 mmol) of phthalic anhydride. After the evolution of gas has subsided, the reaction mixture is taken up in dichloromethane and chromatographed on a silica gel column (eluent: ethyl acetate/petroleum ether/glacial acetic acid 10/10/1).

Yield: 29.6 mg (34.6% of theory)

Melting point: 178° C.

¹H-NMR (DMSO-d₆): 1.3–1.7 (m, 4H); 3.4–3.6 (t, 2H); 3.7–3.8 (m, 1H); 7.5 (d, 2H); 7.7 (d, 2H); 7.7–7.9 (m, 8H); 8.2 (d, 1H, NH); 12.6 (s, 1H, broad, OH)

EXAMPLE 7

2-(2R)-(4-Chlorobiphenylsulfonylamino)-5-(1-oxo-1,3-dihydro-isoindol-2-yl) pentanoic acid 0.32 g (0.76 mmol) of 2-(2R)-(4-chlorobiphenylsulfonylamino)-5-amino-pentanoic acid hydrochloride is dissolved in 30 ml of glacial acetic acid with 0.186 g (1.35 mmol) of phthalaldehyde and stirred at 100° C. for 3 hours. The solution is cooled to 0° C., and the precipitate which is deposited is filtered off with suction and chromatographed on a silica gel column (eluent: ethyl acetate/petroleum ether/glacial acetic acid 10/10/2).

Yield: 185 mg (52% of theory)

Melting point: >234° C. (decomposition) ¹H-NMR (DMSO-d₆): 1.4–1.7 (m, 4H); 3.1 (m, 1H); 3.4–3.6 (m, 2H); 4.4 (d, 1H); 4.5 (d, 1H); 6.9 (s, 1H, broad, OH); 7.4–7.9 (m, 13H)

EXAMPLE 8

R-(4-Biphenylethylsulfonyl)-Lys-OH

Prepared according to process variant e): α-Fmoc-ε-Teoc-D-Lys-OH (0.18 mmol) is coupled under the abovementioned conditions to 100 mg of (0.05 mmol) Wang resin, and after removal of the α-Fmoc protective group is reacted with 0.18 mmol of 4-biphenylethylsulfonyl chloride/diisopropylethylamine. After removal of the ε-Teoc protective group with 1-molar tetrabutylammonium fluoride/DMF solution and removal of the resulting lysine derivative from the resin (trifluoroacetic acid (TFA)/H₂O/triisopropylsilane, 95/2/3), the resulting solution is evaporated. The solid residue is washed with diethyl ether, dissolved in a 10% strength aqueous acetic acid and lyophilized to dryness, and yields 20 mg of the title compound in the form of an amorphous white powder.

HPLC (RP 18; UV 210 nm): Gradient 0–15 min. B=5–70% (A=100% H₂O/0.1% trifluoroacetic acid; B=100% acetonitrile/0.1% trifluoroacetic acid)

T$_R$=9.49 min. (95%)

EXAMPLE 9

R-(4-Biphenylethylsulfonyl)-N-epsilon-acetyl-Lys-OH

As described in Example 8, 0.35 mmol of α-Fmoc-epsilon-Teoc-D-lysine is coupled to 200 mg (0.10 mmol) of Wang resin, Fmoc deprotected and reacted with 4-biphenylethylsulfonyl chloride/diisopropylethylamine. After removal of the ε-Teoc protective group, the resulting lysine derivative is stirred at room temperature for 15 hours with 0.15 mmol of acetic anhydride/0.15 mmol of diisopropylethylamine. After thorough washing with DMF, dichloromethane and drying of the resin (0.1 mm Hg) overnight, the desired compound is removed from the solid support using trifluoroacetic acid/H₂O/triisopropylsilane=95/2/3 and worked up as in Example 8 above. 40 mg of the compound are obtained as an amorphous white powder.

HPLC (RP 18; UV 210 nm): Gradient 0–15 min. B=5–70% (A=100% H₂O/0.1% trifluoroacetic acid; B=100% acetonitrile/0.1% trifluoroacetic acid)

T$_R$=10.39 min. (93%)

The examples mentioned in Table 1 which follows have been prepared analogously to the preceding examples.

TABLE 1

| Ex. | Structure | M.P. (° C.) | MS (M + H) | Notes |
|---|---|---|---|---|
| 1 | 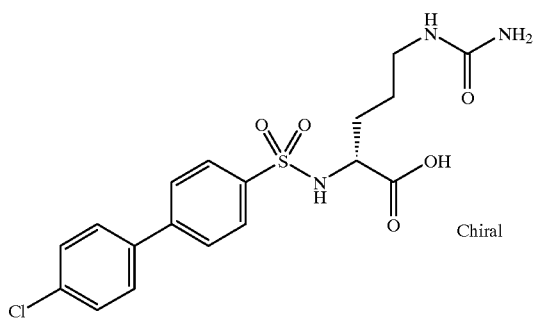 | | 426.1 | R isomer |

TABLE 1-continued
| Ex. | Structure | M.P. (° C.) | MS (M + H) | Notes |
|---|---|---|---|---|
| 2 | 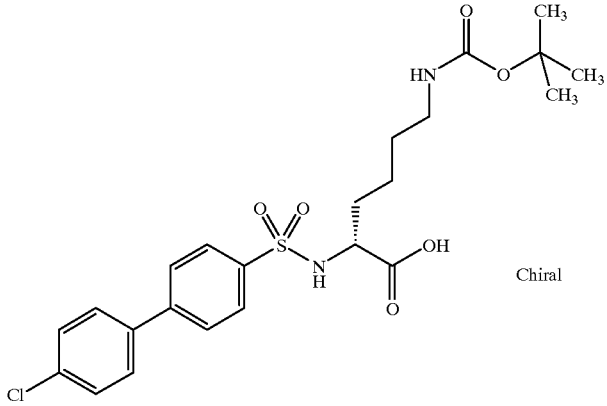 Chiral | | 497.2 | R isomer |
| 3 | 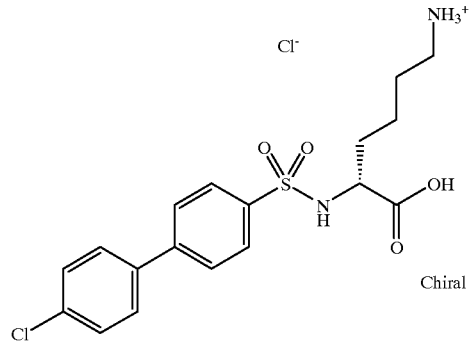 Chiral | | 397.2 | R isomer |
| 4 | 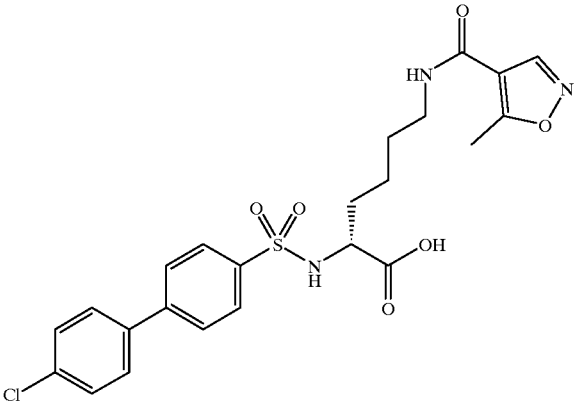 | | 506.1 | R isomer |

TABLE 1-continued
| Ex. | Structure | M.P. (° C.) | MS (M + H) | Notes |
|---|---|---|---|---|
| 5 | 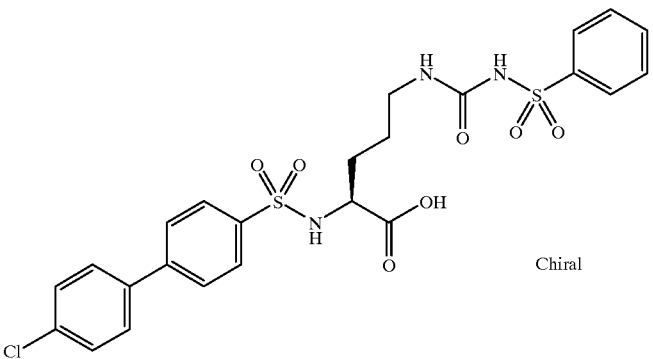 |  | 588.2 (M + Na) | S isomer |
| 6 | 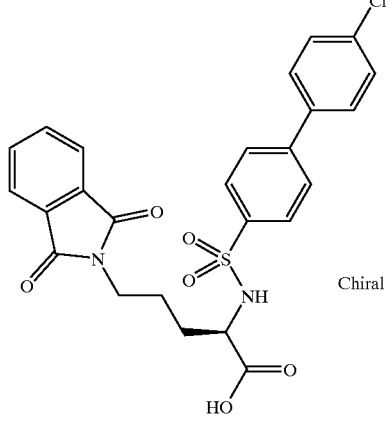 | 178 | 513.2 | R isomer |
| 7 | 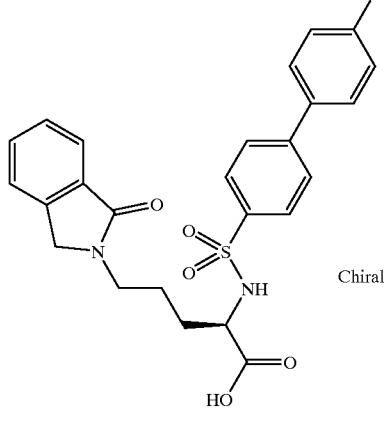 | 233–35 | 521.1 (M + Na) | R isomer |

TABLE 1-continued
| Ex. | Structure | M.P. (° C.) | MS (M + H) | Notes |
|---|---|---|---|---|
| 8 | 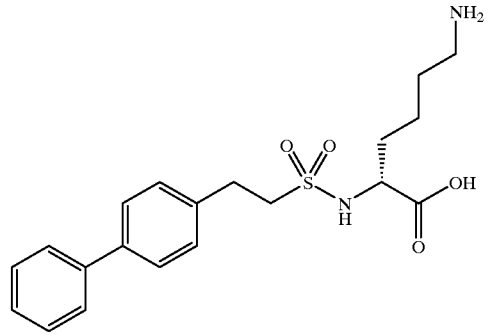 | | 391.2 (M + H) | R isomer |
| 9 | 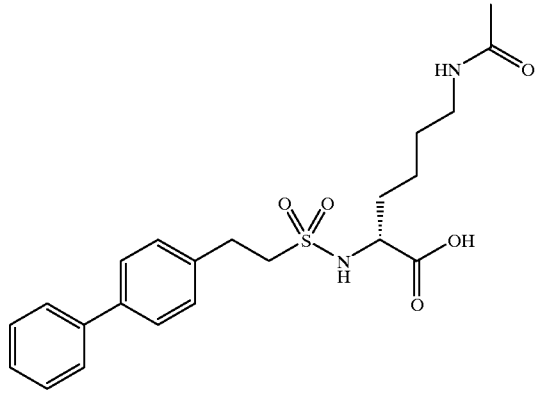 | | 433.2 (M + H) | R isomer |
| 10 | 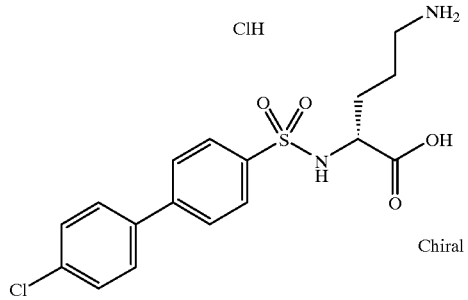 | | 383.1 | R isomer |
| 11 | 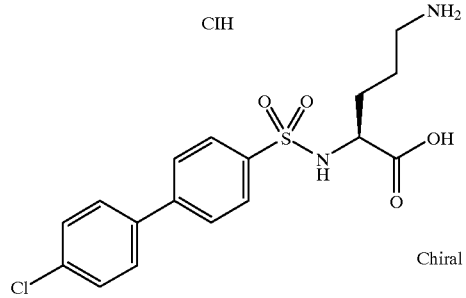 | | 383.1 | S isomer |

TABLE 1-continued
| Ex. | Structure | M.P. (° C.) | MS (M + H) | Notes |
|---|---|---|---|---|
| 12 | 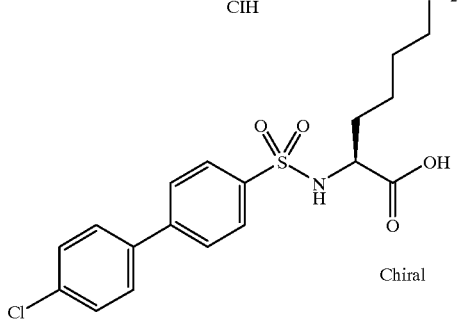 | | 397.2 | S isomer |
| 13 | 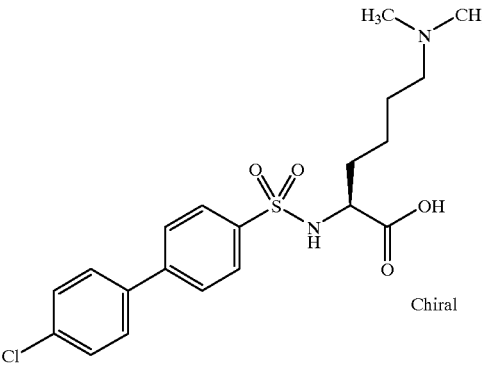 | | 425.2 | S-isomer |
| 14 | 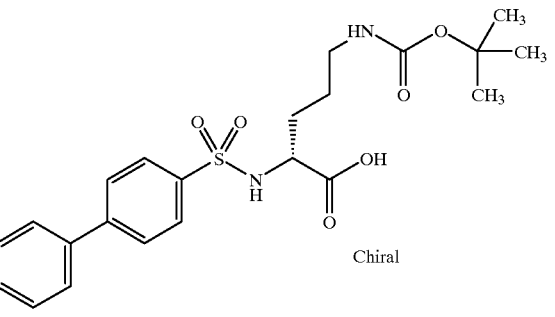 | | 483.2 | R isomer |
| 15 | 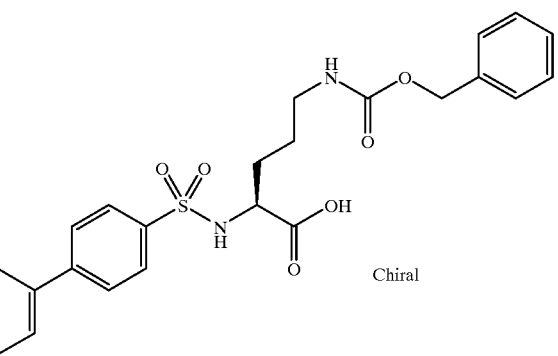 | | 517.1 | S isomer |

TABLE 1-continued
| Ex. | Structure | M.P. (° C.) | MS (M + H) | Notes |
|---|---|---|---|---|
| 16 | 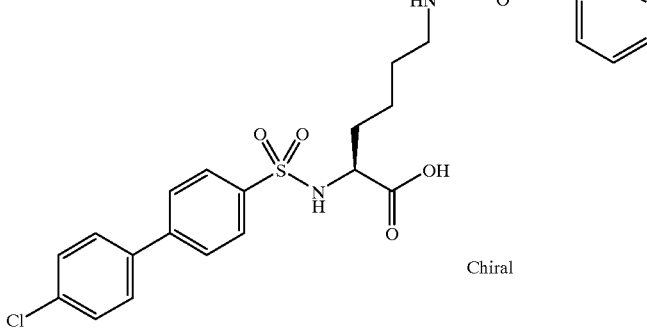 Chiral | | 529.2 (M − 1) | S isomer |
| 17 | 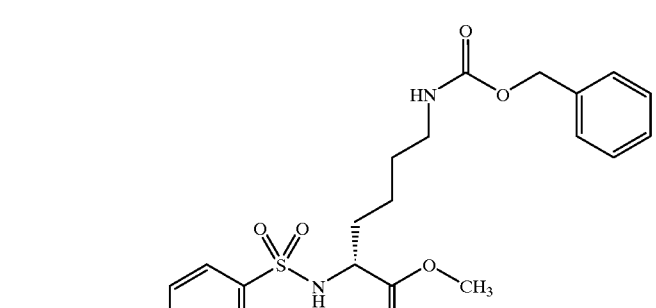 Chiral | 69–70 | | R isomer |
| 18 | 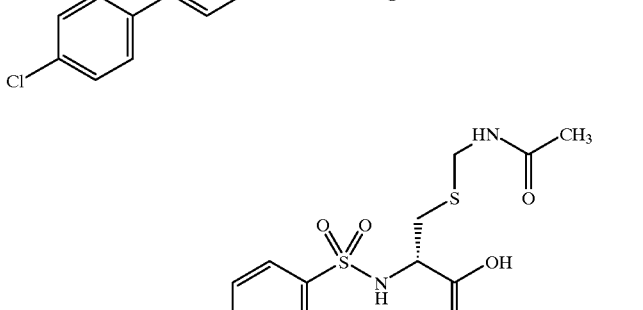 Chiral | | 443.1 | R isomer |
| 19 |  Chiral | | 489.1 | S isomer |

TABLE 1-continued

| Ex. | Structure | M.P. (° C.) | MS (M + H) | Notes |
|---|---|---|---|---|
| 20 | 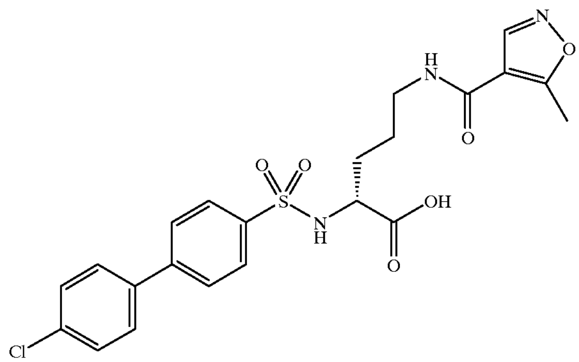 | | 492.1 | R isomer |
| 21 | 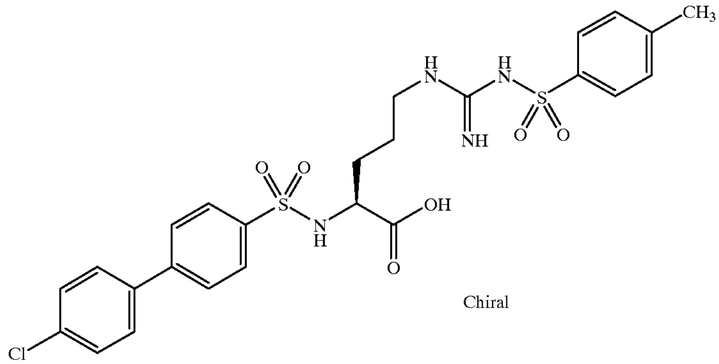 | | 579.2 | S isomer |
| 22 | 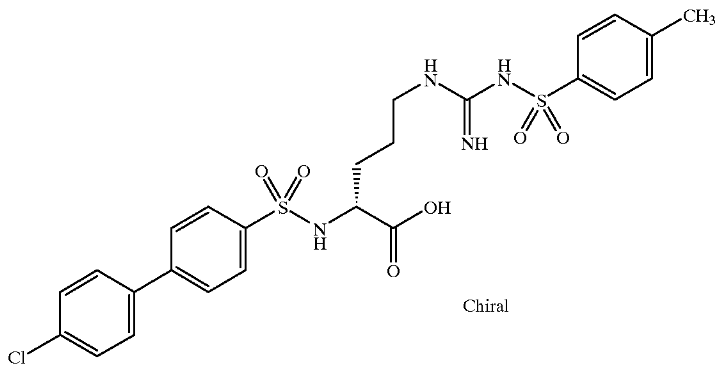 | | 579.2 | R isomer |
| 23 | 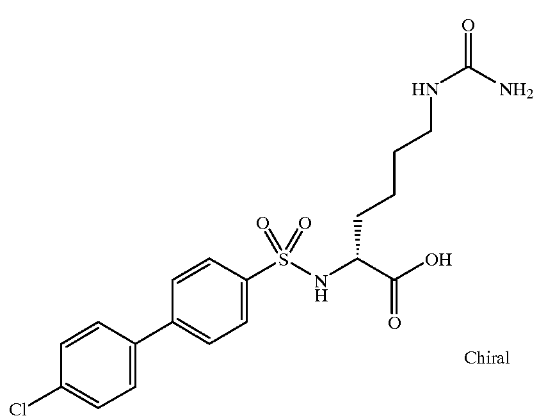 | | 440.1 | R isomer |

TABLE 1-continued
| Ex. | Structure | M.P. (° C.) | MS (M + H) | Notes |
|---|---|---|---|---|
| 24 | 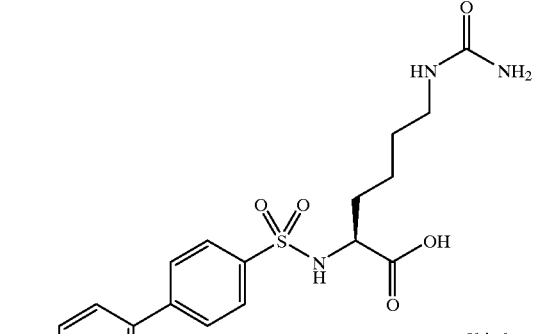 Chiral | | 440.1 | S isomer |
| 25 | 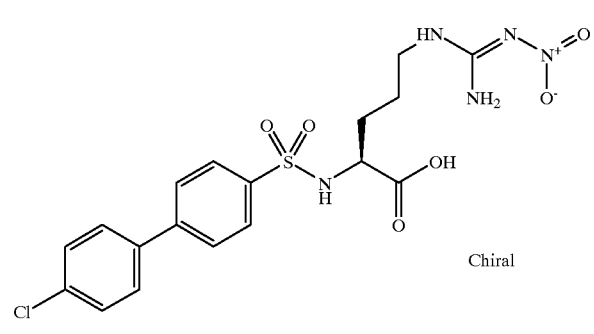 Chiral | | 470.2 | S isomer |
| 26 | 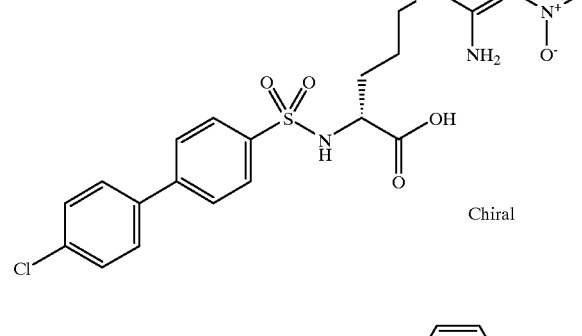 Chiral | | 470.2 | R isomer |
| 27 | 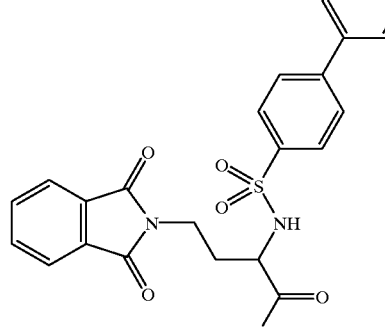 | 176 | 465.1 | racemate |

TABLE 1-continued
| Ex. | Structure | M.P. (° C.) | MS (M + H) | Notes |
|---|---|---|---|---|
| 28 | 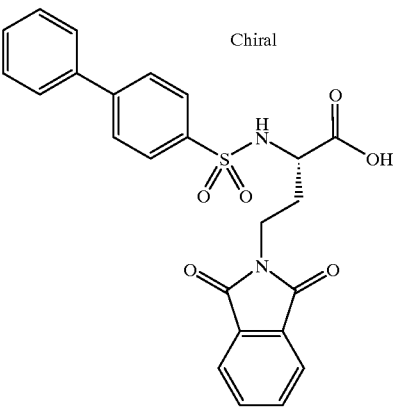 | 167 | 465.2 | S isomer |
| 29 | 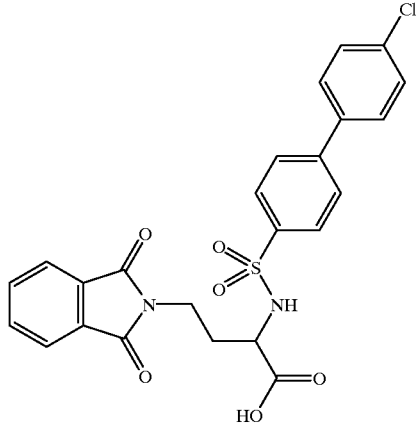 | 238 | 499.2 | racemate |
| 30 | 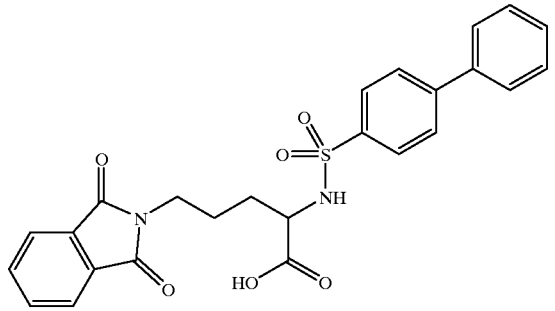 | 168 | 479.2 | racemate |

TABLE 1-continued

| Ex. | Structure | M.P. (° C.) | MS (M + H) | Notes |
|---|---|---|---|---|
| 31 | 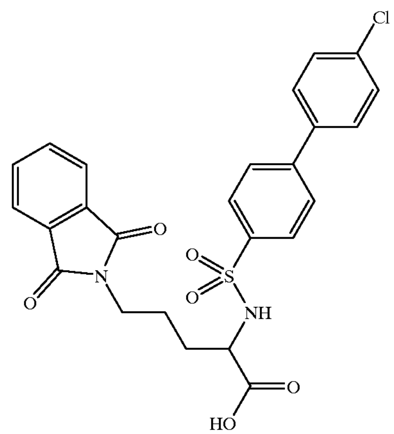 | 132 | 513.2 | racemate |
| 32 | 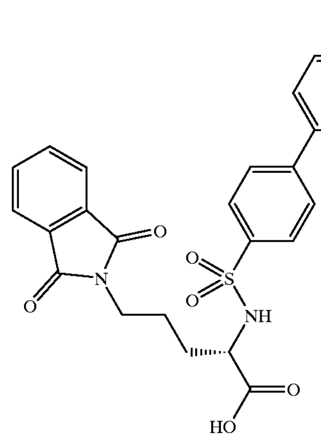 | 179 | 513.2 | S isomer |
| 33 | 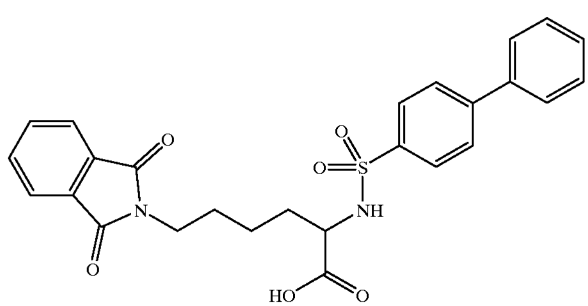 | 181 | 493.2 | racemate |

TABLE 1-continued

| Ex. | Structure | M.P. (° C.) | MS (M + H) | Notes |
|---|---|---|---|---|
| 34 | 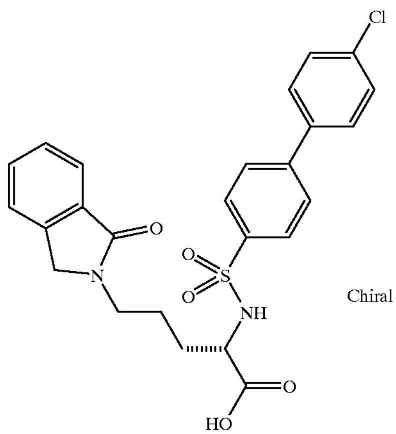 | 213–15 | 521.1 (M + Na) | S isomer |
| 35 | 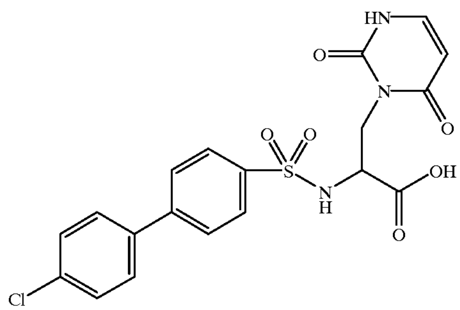 | | 450.1 | racemate |
| 36 | 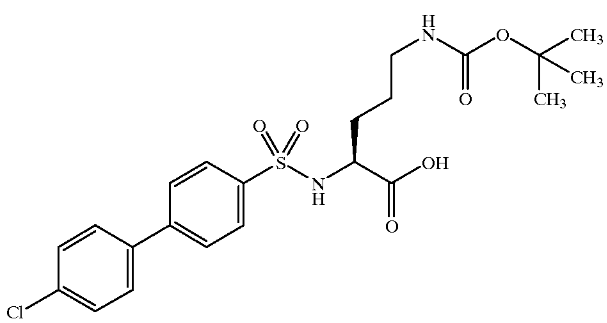 | | 483.1 | S |
| 37 | 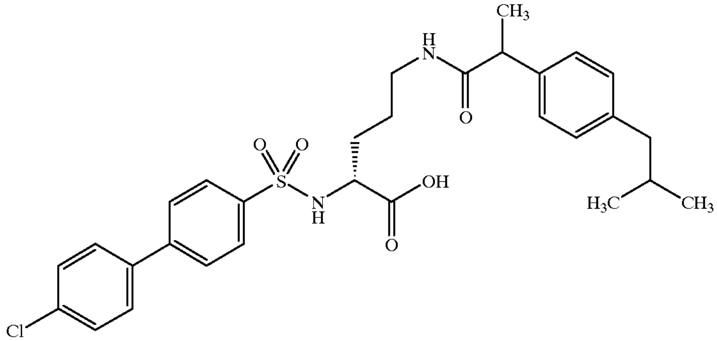 | | 571.2 | R,S/R,R |

TABLE 1-continued
| Ex. | Structure | M.P. (° C.) | MS (M + H) | Notes |
|---|---|---|---|---|
| 38 | 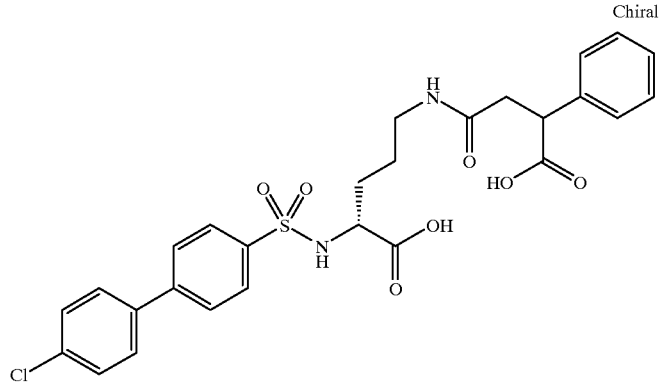 | | 559.1 | R(A) |
| 39 | 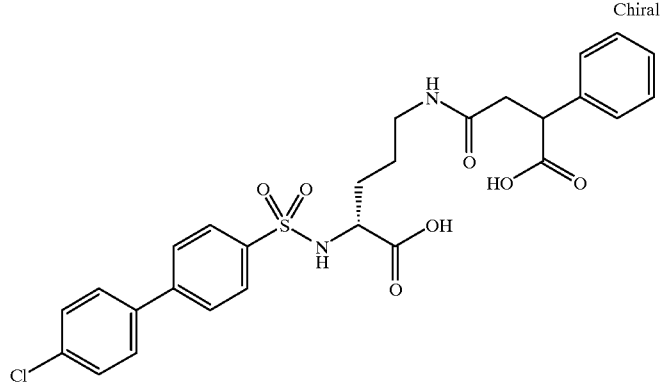 | | 559.2 | R(B) |
| 40 | 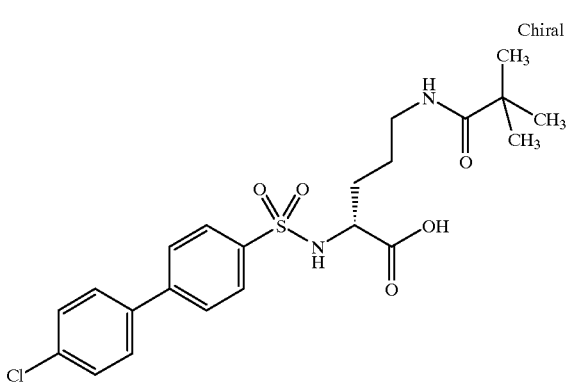 | | 467.2 | R |
| 41 | 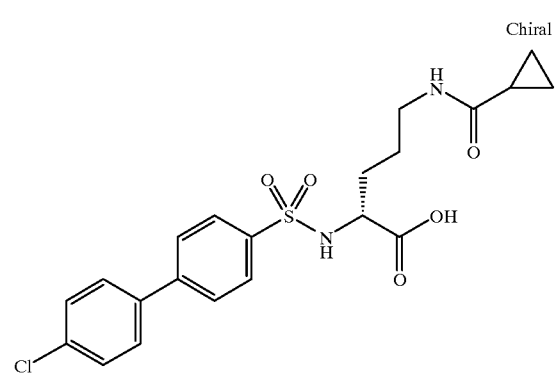 | | 451.2 | R |

TABLE 1-continued
| Ex. | Structure | M.P. (° C.) | MS (M + H) | Notes |
|---|---|---|---|---|
| 42 | 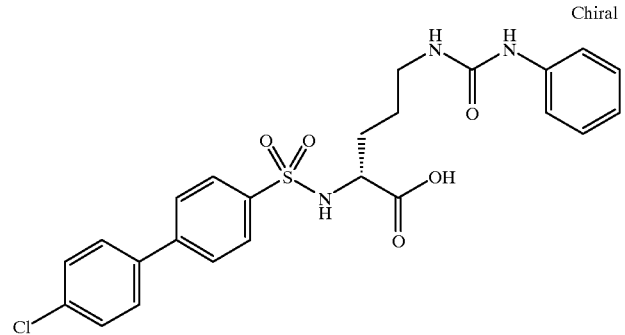 | | 502.2 | R |
| 43 | 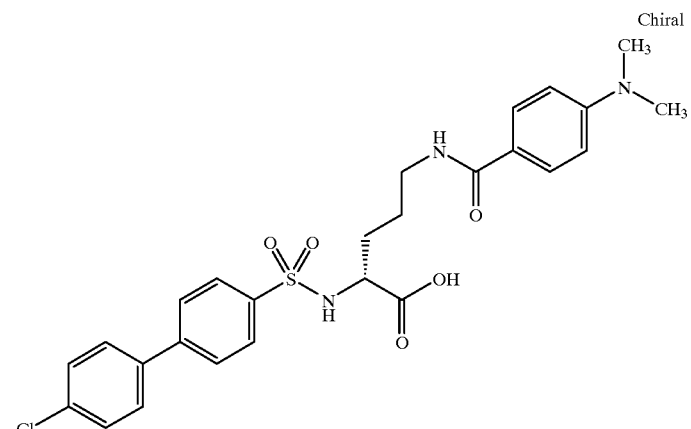 | | 530.1 | R |
| 44 | 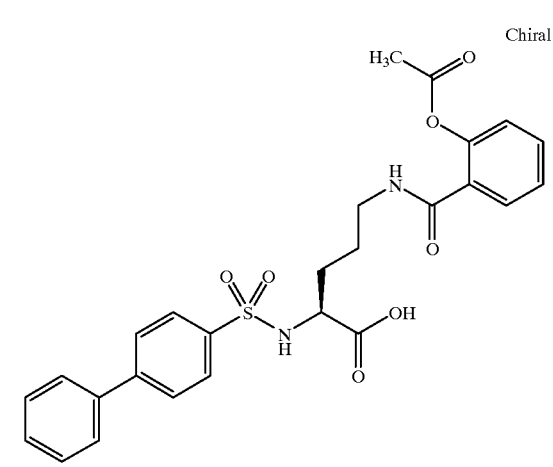 | | 511.2 | S |

TABLE 1-continued
| Ex. | Structure | M.P. (° C.) | MS (M + H) | Notes |
|---|---|---|---|---|
| 45 | 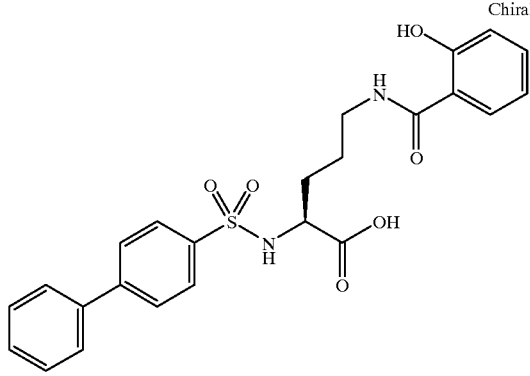 | | 469.2 | S |
| 46 | 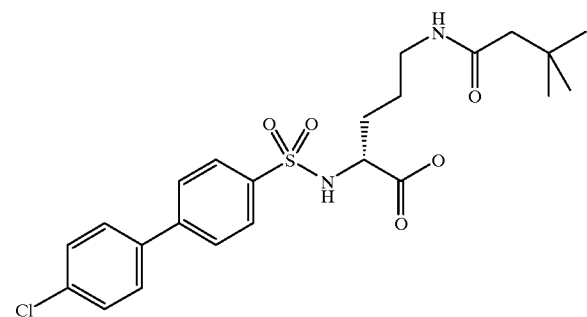 | | 481.2 | R |
| 47 | 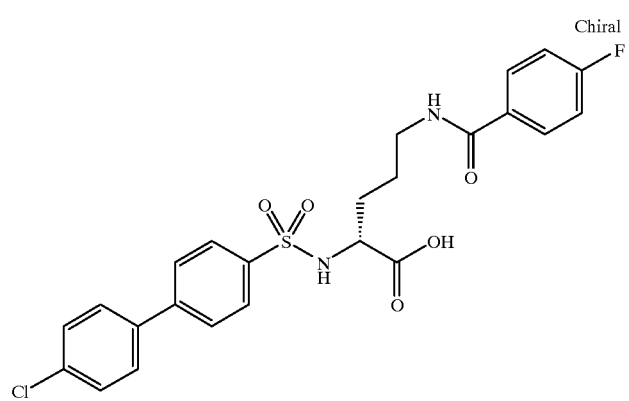 | | 505.2 | R |
| 48 | 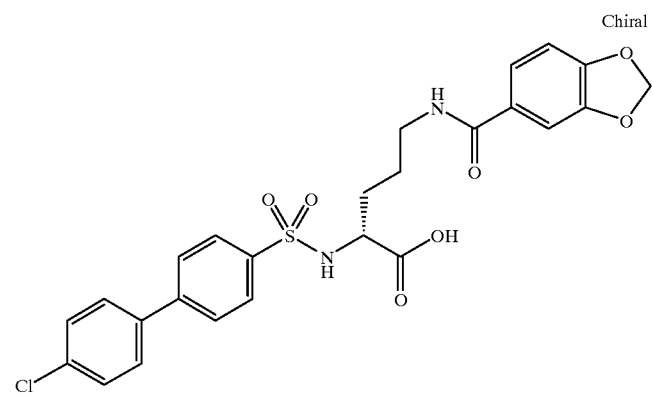 | | 531.2 | R |

TABLE 1-continued
| Ex. | Structure | M.P. (° C.) | MS (M + H) | Notes |
|---|---|---|---|---|
| 49 | 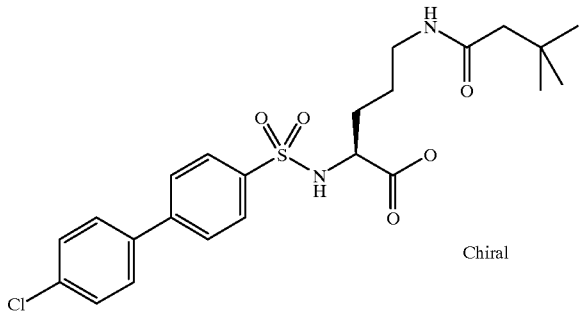 | | 481.1 | S |
| 50 | 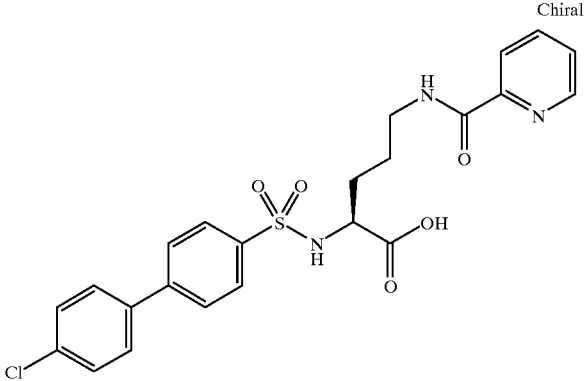 | | 488.1 | S |
| 51 | 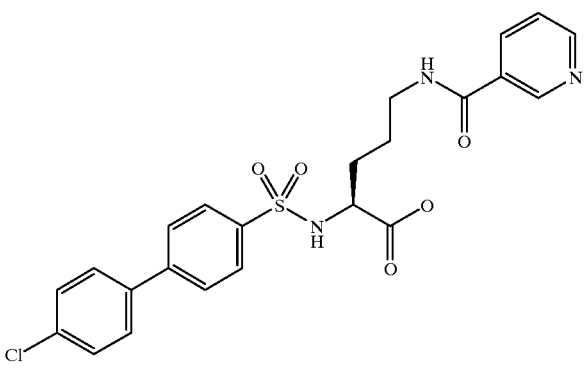 | | 488.1 | S |
| 52 | 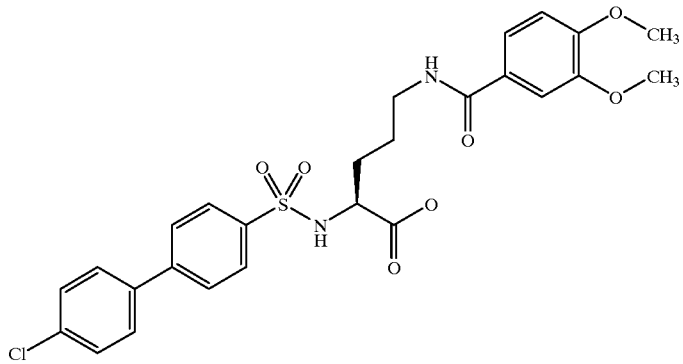 | | 547.2 | S |

TABLE 1-continued

| Ex. | Structure | M.P. (° C.) | MS (M + H) | Notes |
|---|---|---|---|---|
| 53 | 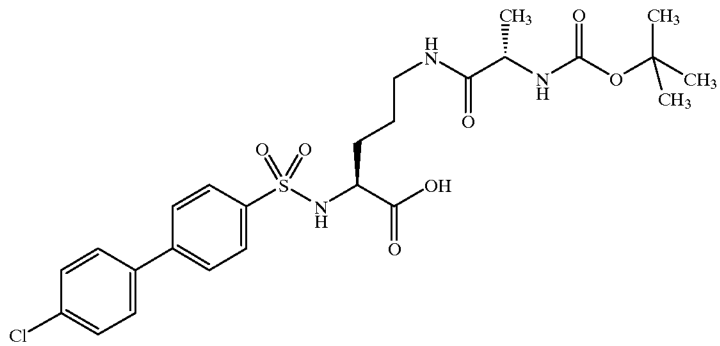 | | 554.2 | S,S |
| 54 | 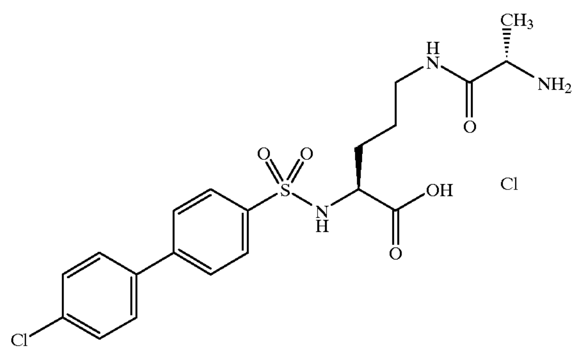 | | 454.2 | S,S |
| 55 | 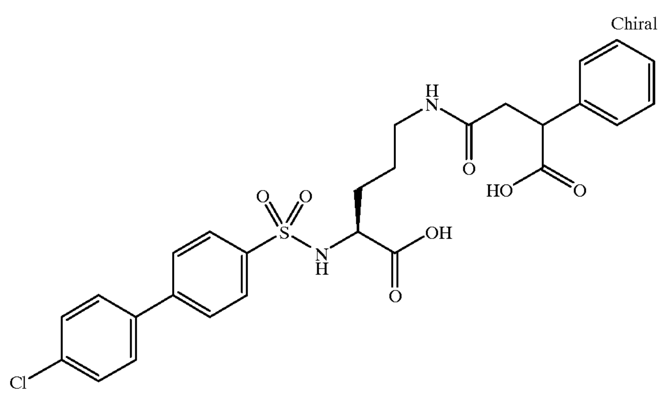 | | 559.2 | S,R/S,S |
| 56 | 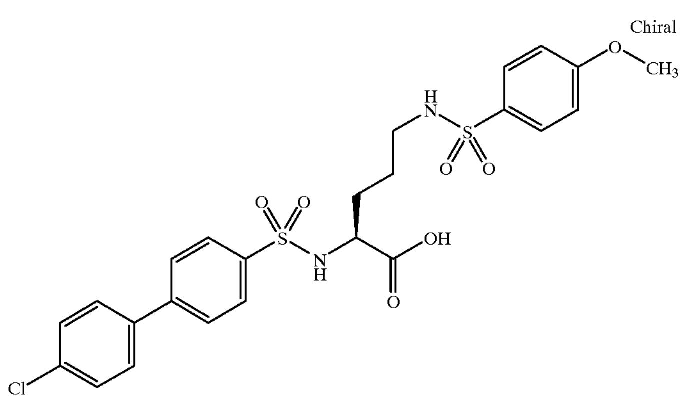 | | 553.1 | S |

TABLE 1-continued
| Ex. | Structure | M.P. (° C.) | MS (M + H) | Notes |
|---|---|---|---|---|
| 57 | 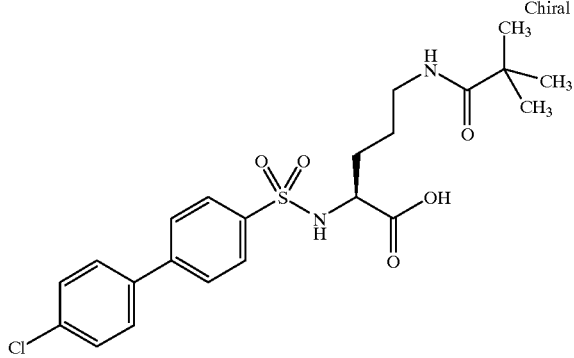 | | 467.2 | S |
| 58 | 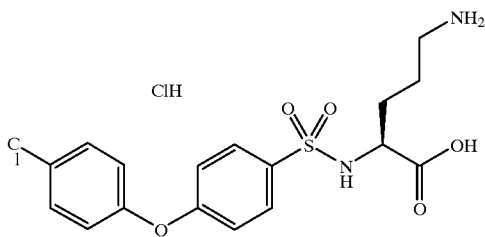 | | 399.2 | S |
| 59 | 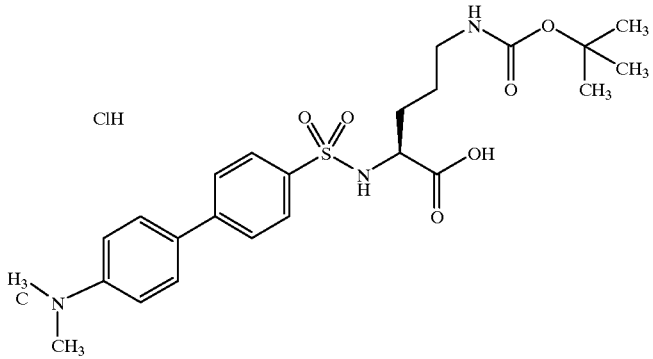 | | 492.3 | S |
| 60 | 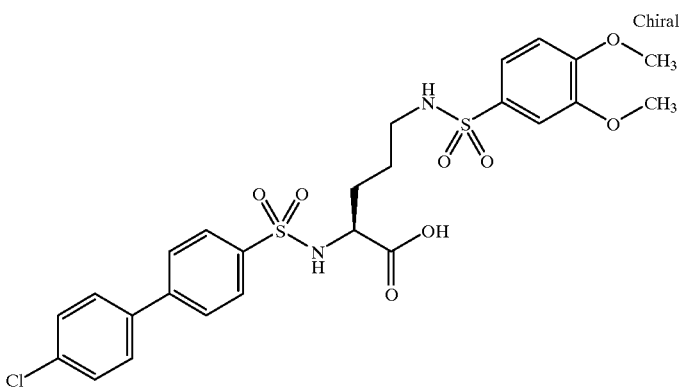 | | 583.1 | S |

TABLE 1-continued

| Ex. | Structure | M.P. (° C.) | MS (M + H) | Notes |
|---|---|---|---|---|
| 61 | 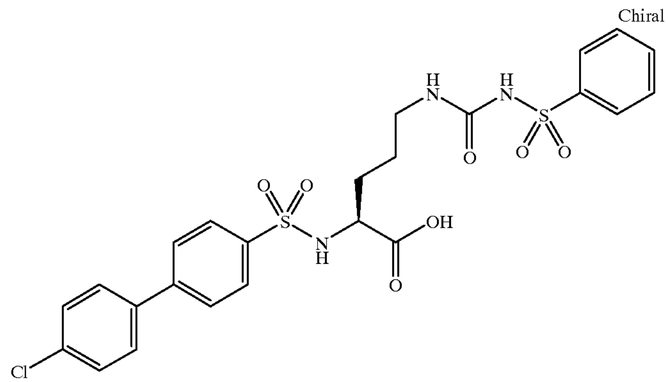 | | 566.2 | S |
| 62 | 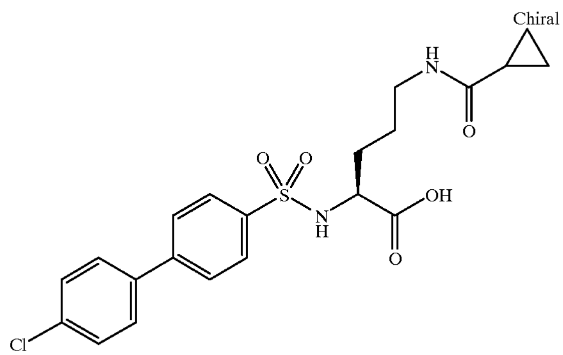 | | 451.2 | S |
| 63 | 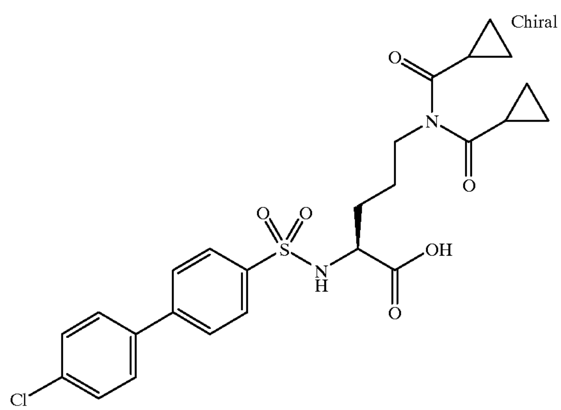 | | 519.2 | S |
| 64 | 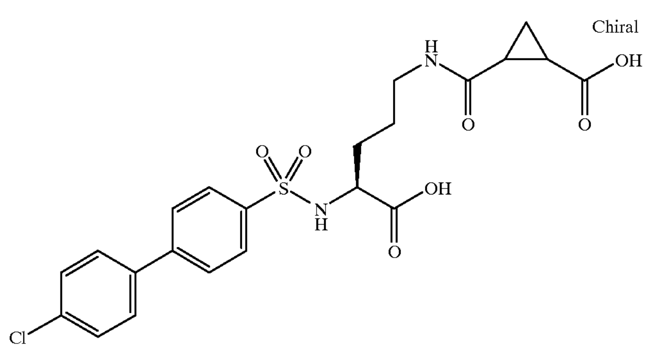 | | 495.2 | S |

TABLE 1-continued
| Ex. | Structure | M.P. (° C.) | MS (M + H) | Notes |
|---|---|---|---|---|
| 65 | 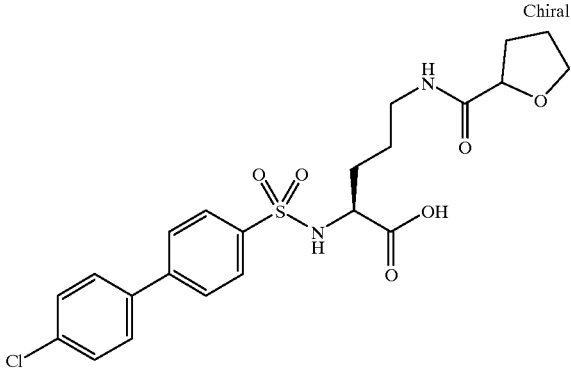 | | 479.2 | S |
| 66 | 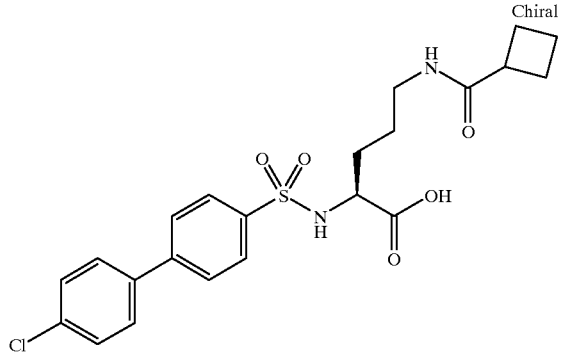 | | 465.2 | S |
| 67 | 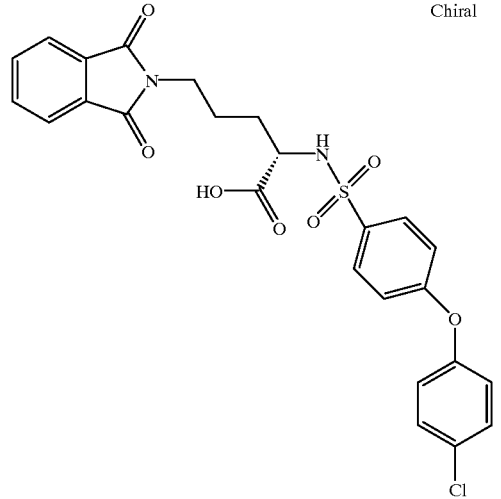 | | 529.2 | S |

TABLE 1-continued

| Ex. | Structure | M.P. (° C.) | MS (M + H) | Notes |
|---|---|---|---|---|
| 68 | Chiral | 223–225°°C. | | S |
| 69 | Chiral | | 465.2 | "S" |
| 70 | Chiral | | 507.3 | S |

TABLE 1-continued
| Ex. | Structure | M.P. (° C.) | MS (M + H) | Notes |
|---|---|---|---|---|
| 71 | 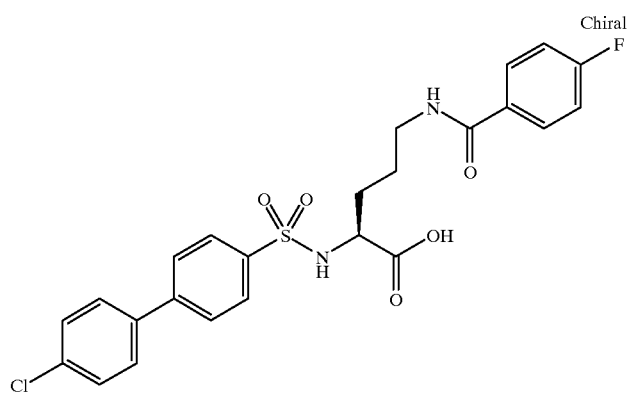 | | 505.1 | S |
| 72 | 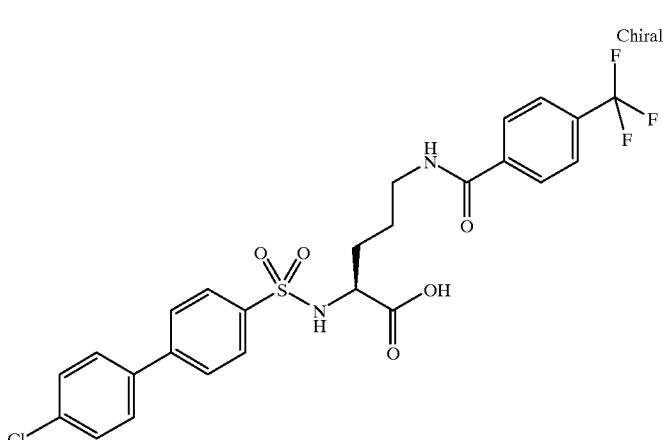 | | 555.1 | S |
| 73 | 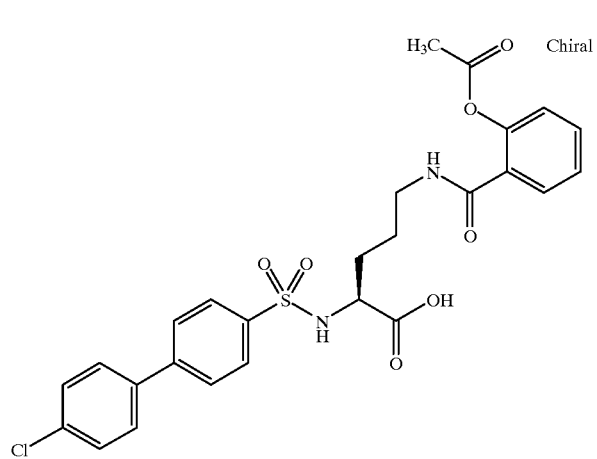 | | 545.2 | S |

TABLE 1-continued
| Ex. | Structure | M.P. (° C.) | MS (M + H) | Notes |
|---|---|---|---|---|
| 74 | 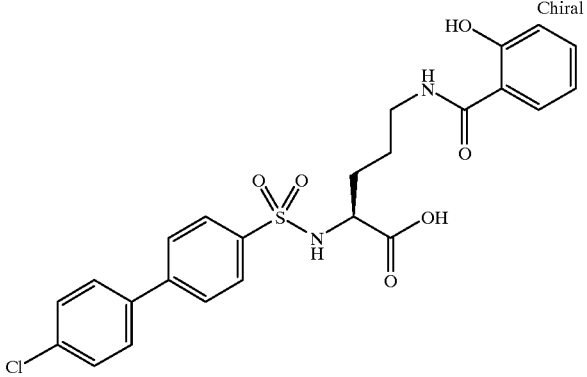 |  | 503.1 | S |
| 75 | 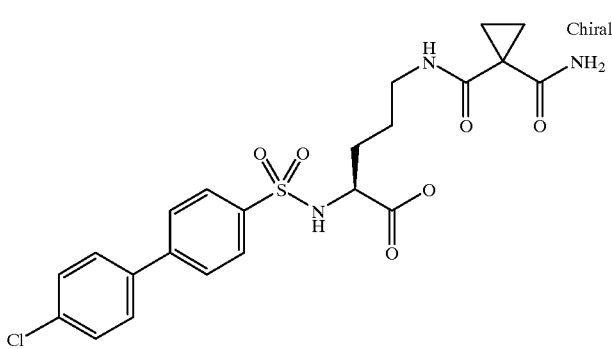 |  | 494.1 | S |
| 76 | 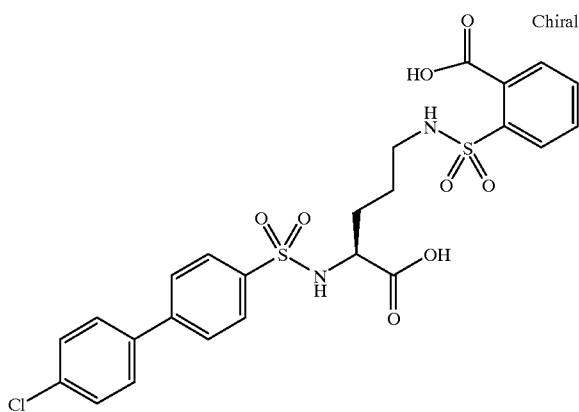 |  | 565.2 M − H | S |
| 77 | 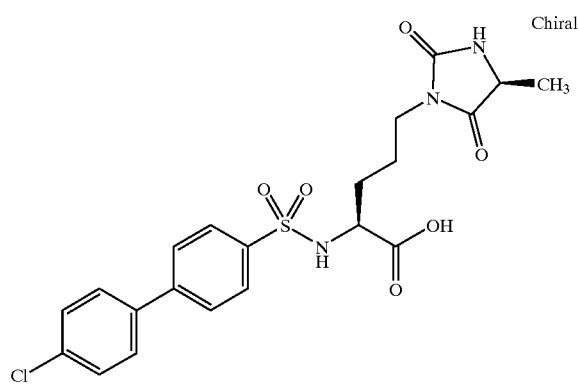 |  | 480.2 | S |

TABLE 1-continued

| Ex. | Structure | M.P. (° C.) | MS (M + H) | Notes |
|---|---|---|---|---|
| 78 | 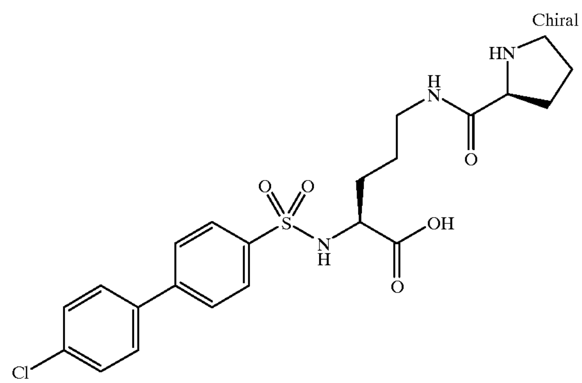 | | 478.2 | S |
| 79 | 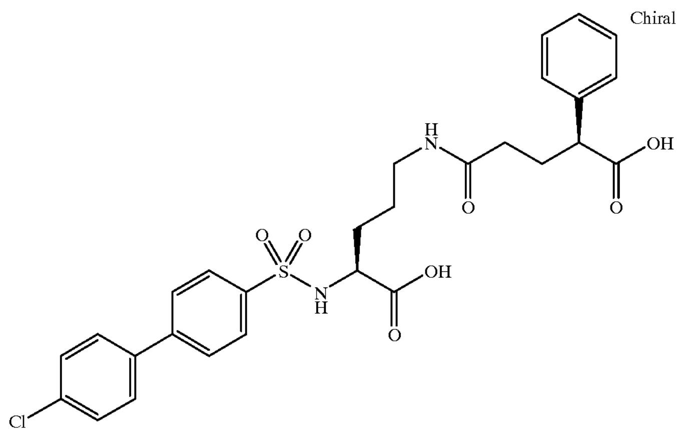 | | 573.1 | S |
| 80 | 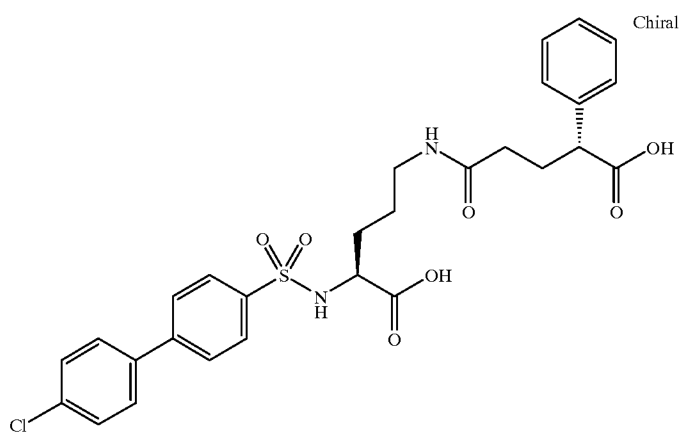 | | 573.1 | S |

6,159,995
TABLE 1-continued
| Ex. | Structure | M.P. (° C.) | MS (M + H) | Notes |
|---|---|---|---|---|
| 81 | 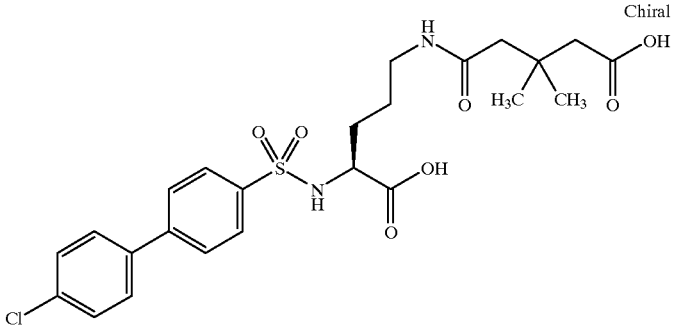 | | 525.2 | S |
| 82 | 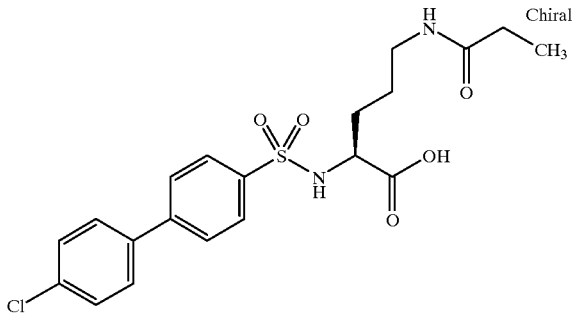 | | 439.1 | S |
| 83 | 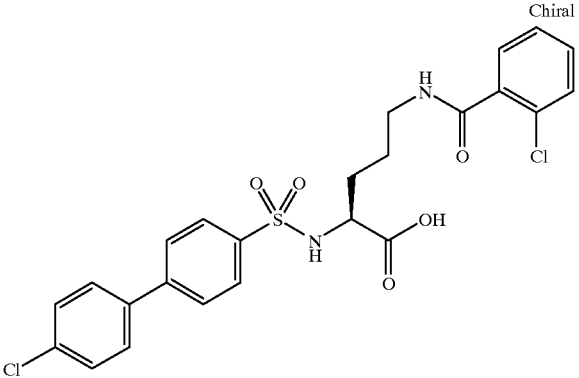 | | 521.2 | S |
| 84 | 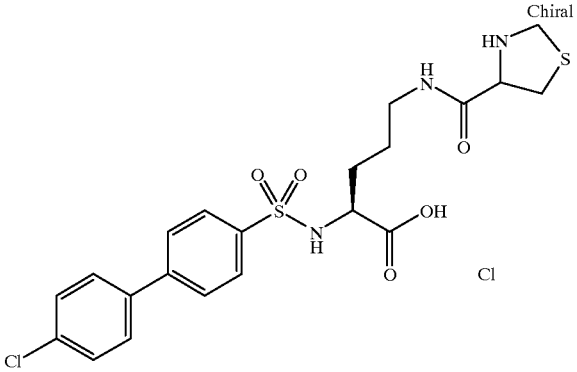 | | 498.2 | S |

TABLE 1-continued
| Ex. | Structure | M.P. (° C.) | MS (M + H) | Notes |
|---|---|---|---|---|
| 85 | 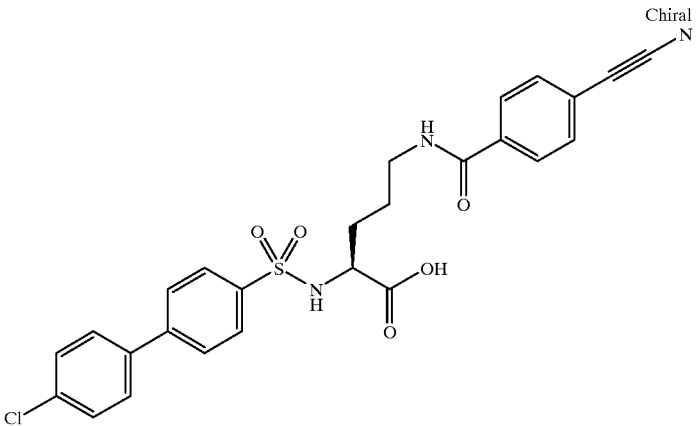 | | 512.2 | S |
| 86 | 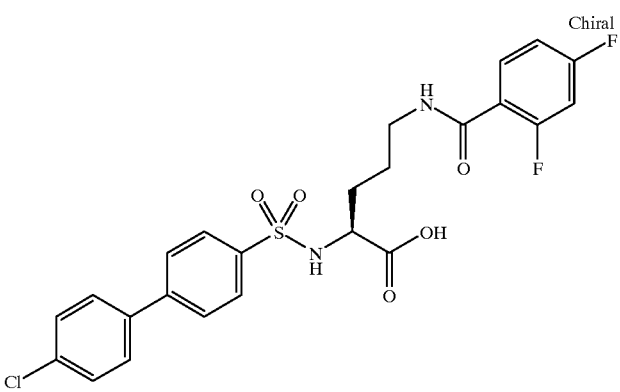 | | 523.2 | S |
| 87 | 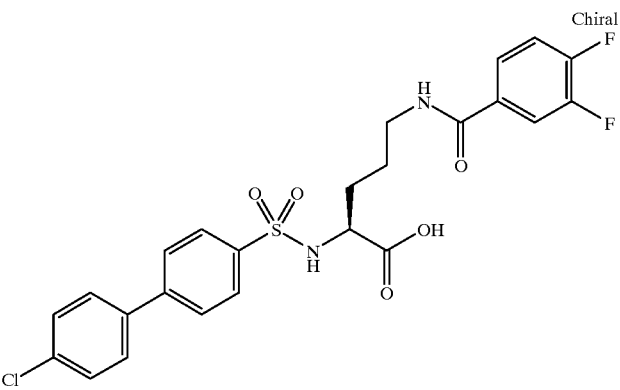 | | 523.2 | S |

TABLE 1-continued
| Ex. | Structure | M.P. (° C.) | MS (M + H) | Notes |
|---|---|---|---|---|
| 88 | 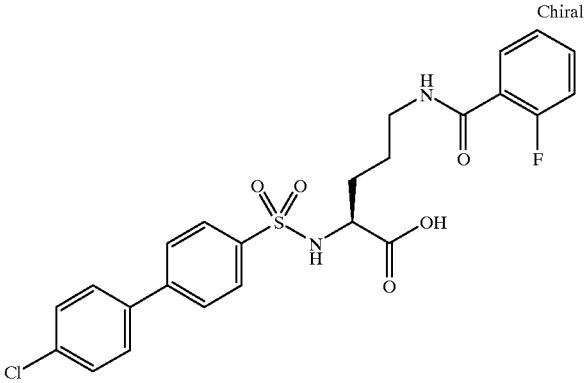 | | 505.2 | S |
| 89 | 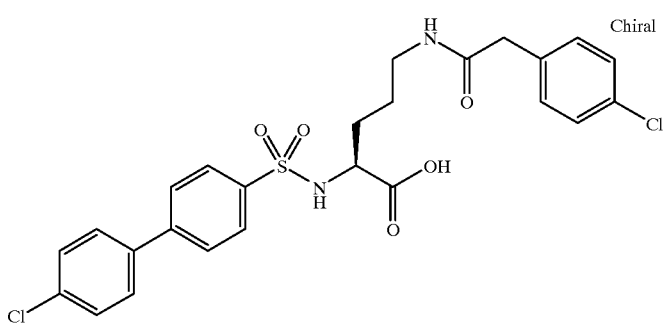 | | 535.2 | S |
| 90 | 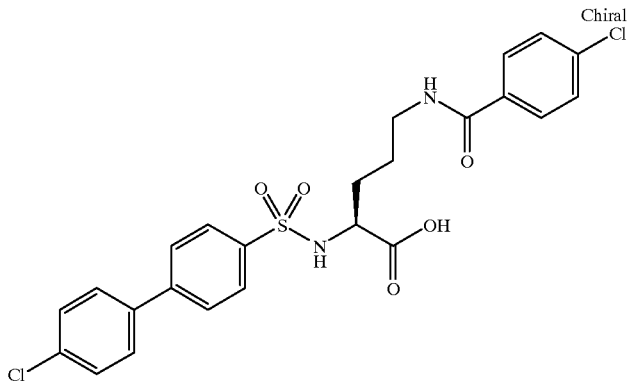 | | 521.2 | S |
| 91 | 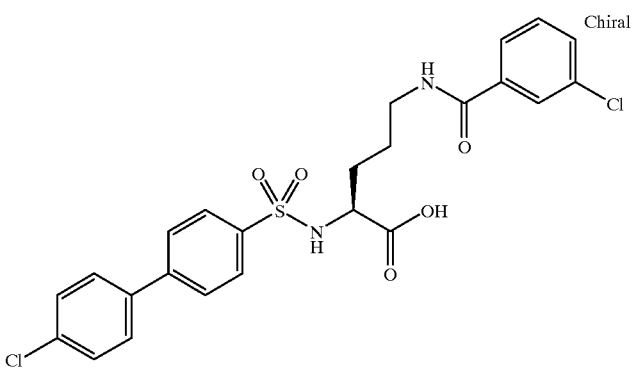 | | 521.2 | S |

TABLE 1-continued
| Ex. | Structure | M.P. (° C.) | MS (M + H) | Notes |
|---|---|---|---|---|
| 92 | 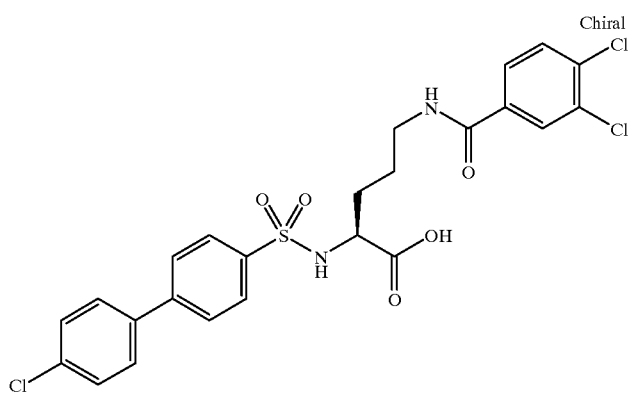 | | 557.1 | S |
| 93 | 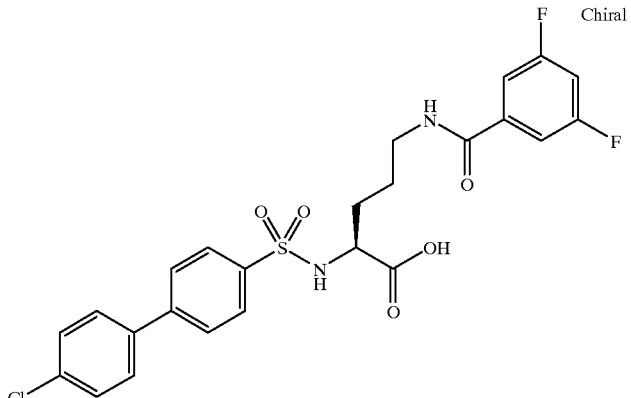 | | 523.2 | S |
| 94 | 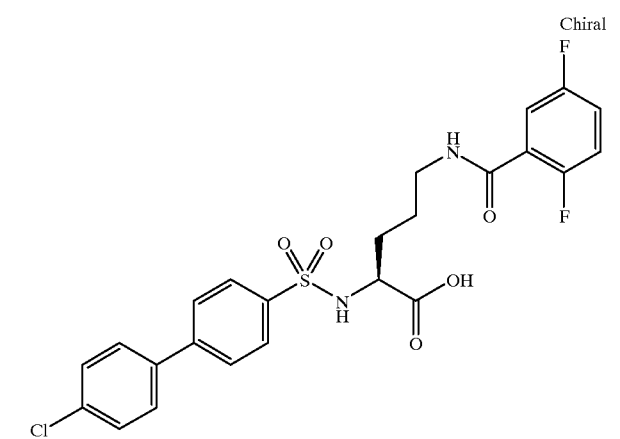 | | 523.2 | S |

TABLE 1-continued

| Ex. | Structure | M.P. (° C.) | MS (M + H) | Notes |
|---|---|---|---|---|
| 95 | 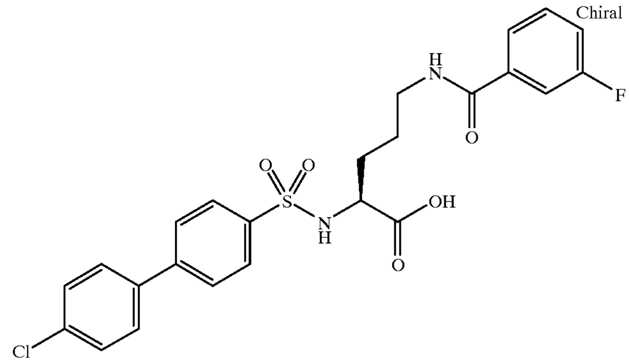 | | 505.2 | S |
| 96 | 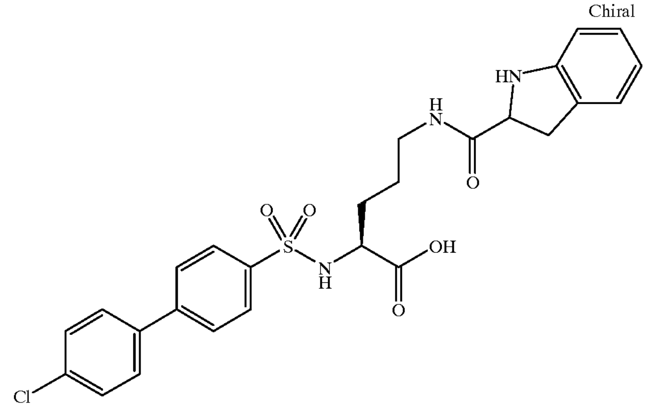 | | 528.2 | S |
| 97 | 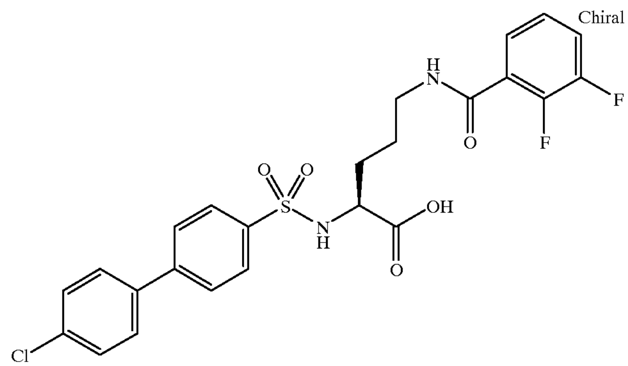 | | 523.2 | S |
| 98 | 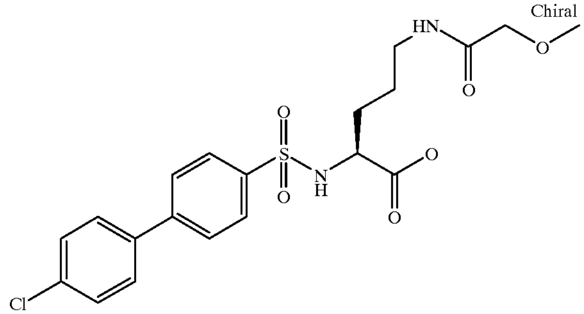 | | 455.2 | S |

6,159,995
TABLE 1-continued
| Ex. | Structure | M.P. (° C.) | MS (M + H) | Notes |
|---|---|---|---|---|
| 99 | 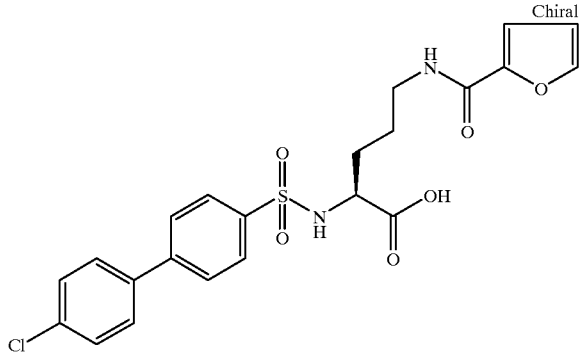 | | 477.2 | S |
| 100 | 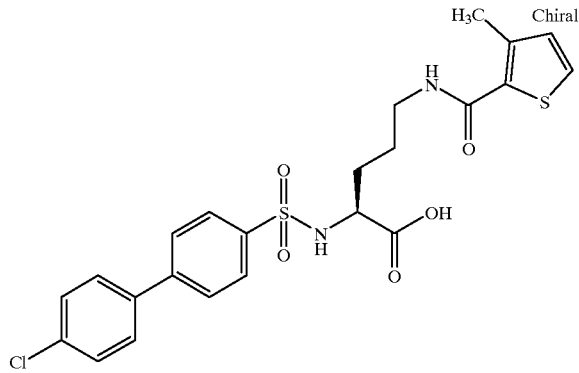 | | 507.2 | S |
| 101 | 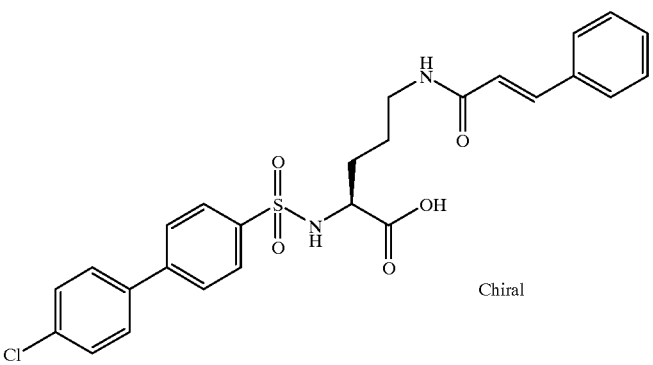 | | 513.2 | S |
| 102 | 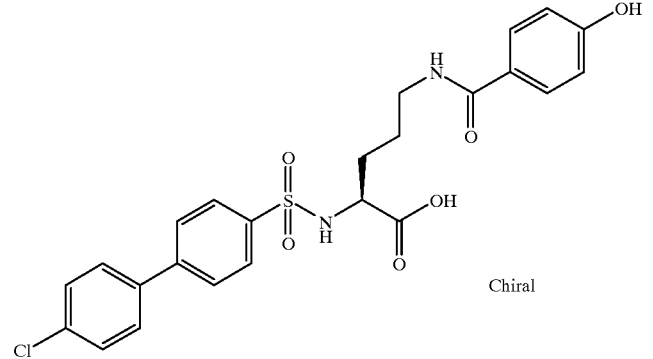 | | 503.2 | S |

TABLE 1-continued
| Ex. | Structure | M.P. (° C.) | MS (M + H) | Notes |
|---|---|---|---|---|
| 103 | 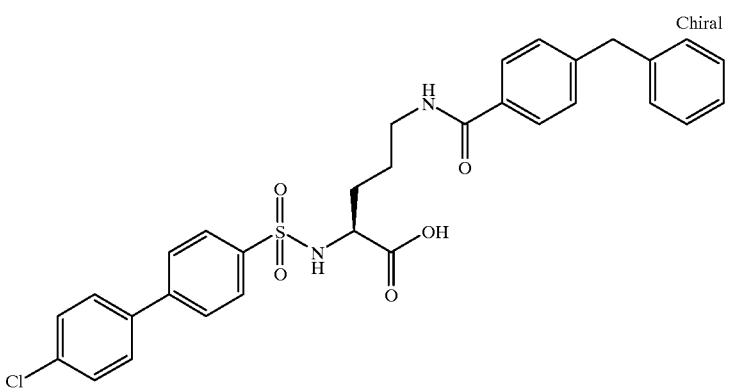 | | 577.2 | S |
| 104 | 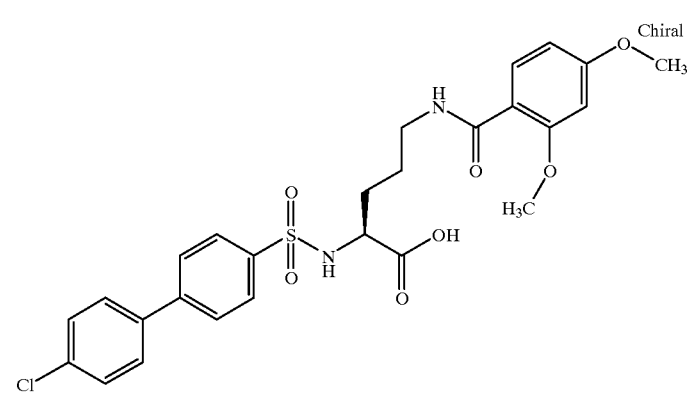 | | 547.2 | S |
| 105 | 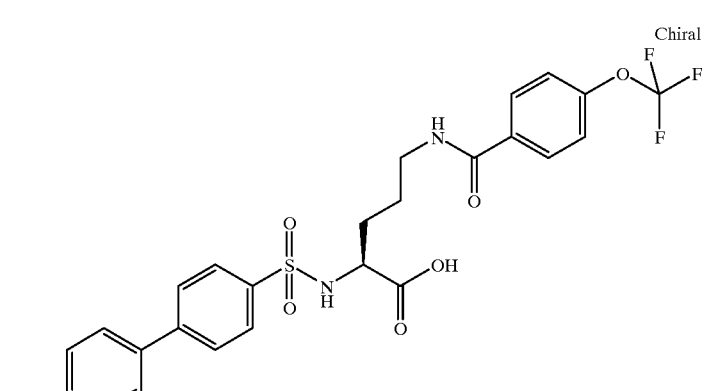 | | 571.2 | S |

TABLE 1-continued

| Ex. | Structure | M.P. (° C.) | MS (M + H) | Notes |
|---|---|---|---|---|
| 106 | 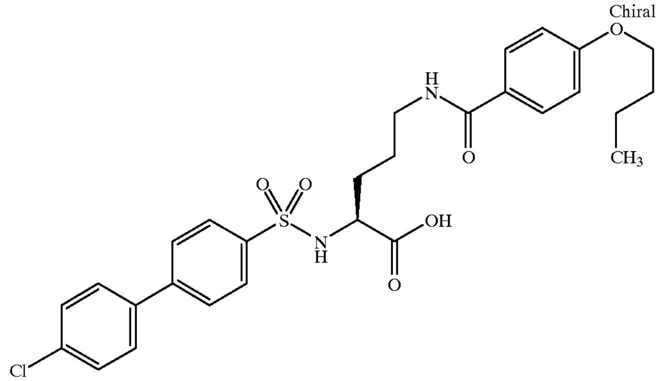 | | 559.2 | S |
| 107 | 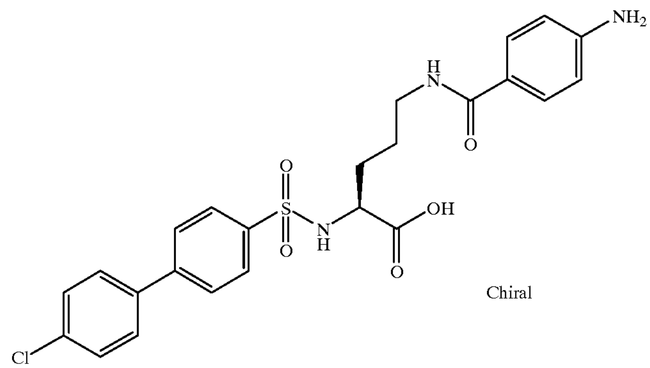 | | 502.2 | S |
| 108 | 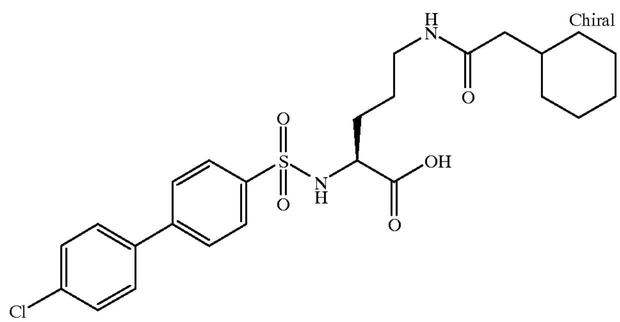 | | 507.2 | S |
| 109 | 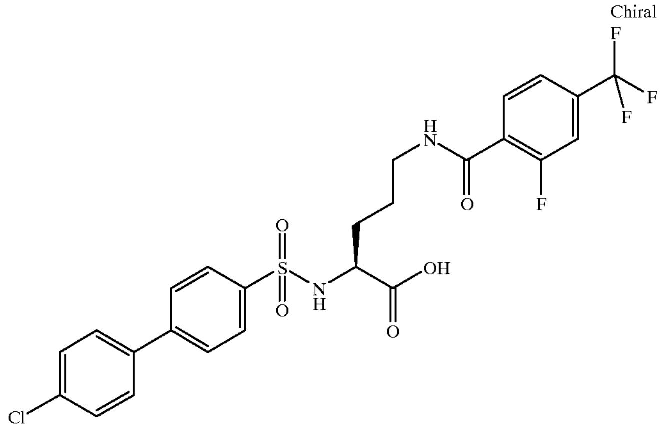 | | 573.2 | S |

TABLE 1-continued
| Ex. | Structure | M.P. (° C.) | MS (M + H) | Notes |
|---|---|---|---|---|
| 110 | 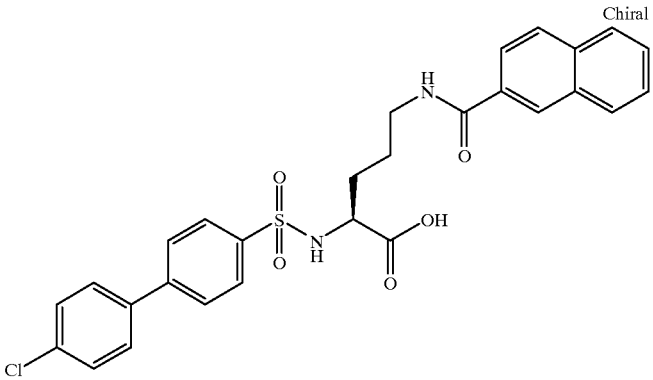 | | 537.2 | S |
| 111 | 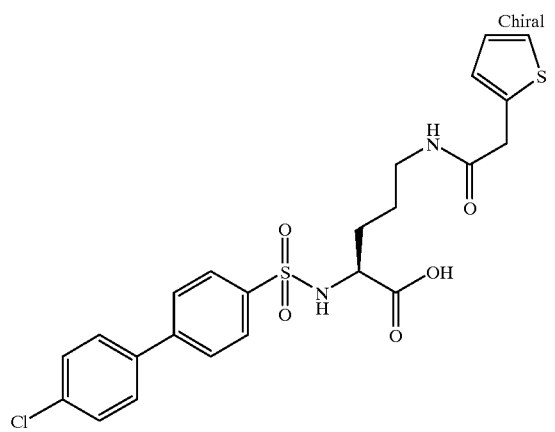 | | 507.2 | S |
| 112 | 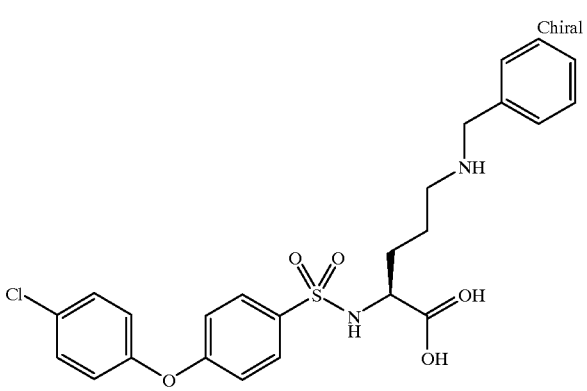 | | 489 | S |

TABLE 1-continued
| Ex. | Structure | M.P. (° C.) | MS (M + H) | Notes |
|---|---|---|---|---|
| 113 | 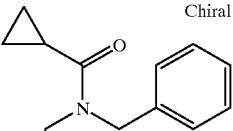 | | 541.3 | S |
| 114 | 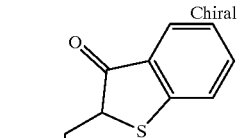 | | 517.03 | S |
| 115 | 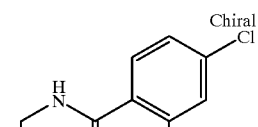 | | 556.1 | S |
| 116 | 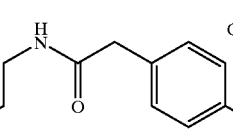 | | 519.2 | S |

TABLE 1-continued

| Ex. | Structure | M.P. (° C.) | MS (M + H) | Notes |
|---|---|---|---|---|
| 117 | 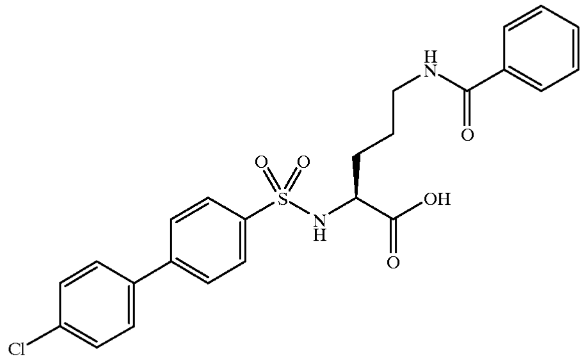 | | 487.2 | S |
| 118 | 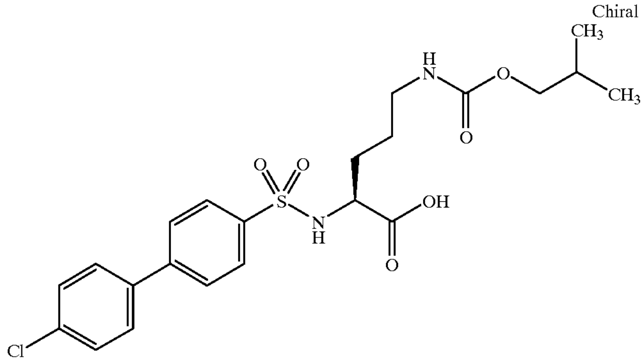 | | 483.3 | S |
| 119 | 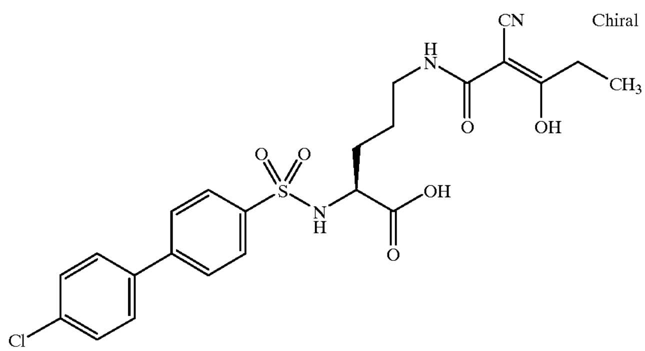 | | 490.3 | S |
| 120 | 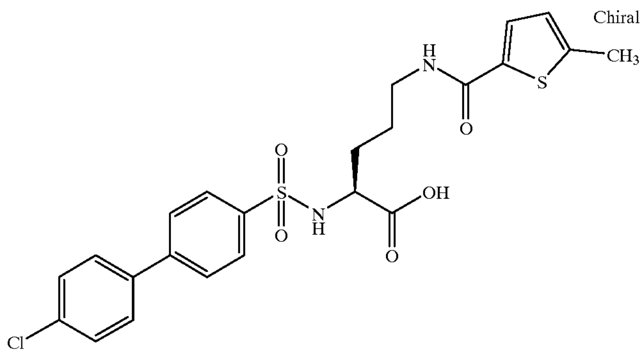 | | 507.2 | S |

TABLE 1-continued
| Ex. | Structure | M.P. (° C.) | MS (M + H) | Notes |
|---|---|---|---|---|
| 121 | 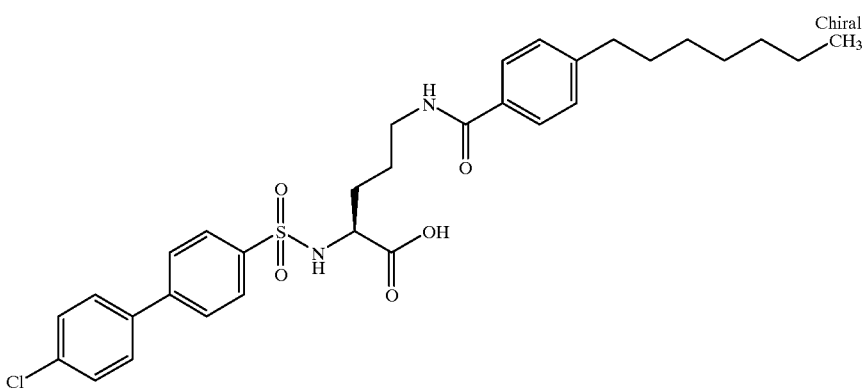 | | 585.3 | S |
| 122 | 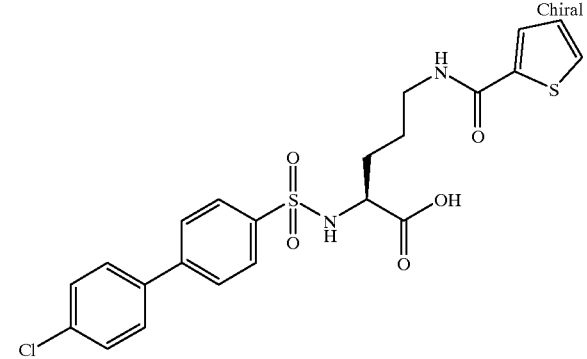 | | 493.2 | S |
| 123 | 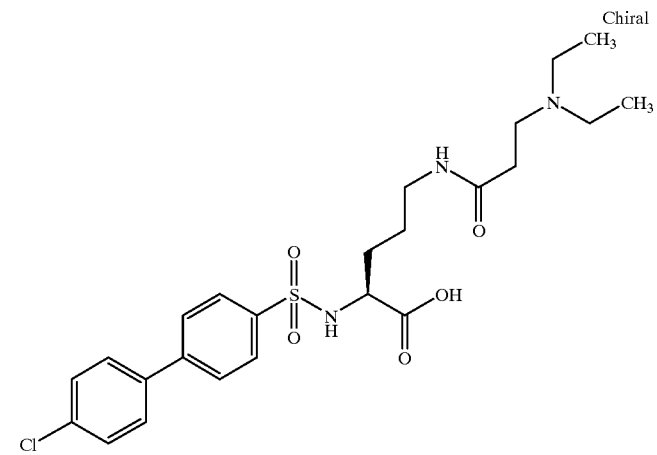 | | 510.3 | S |

TABLE 1-continued
| Ex. | Structure | M.P. (° C.) | MS (M + H) | Notes |
|---|---|---|---|---|
| 124 | 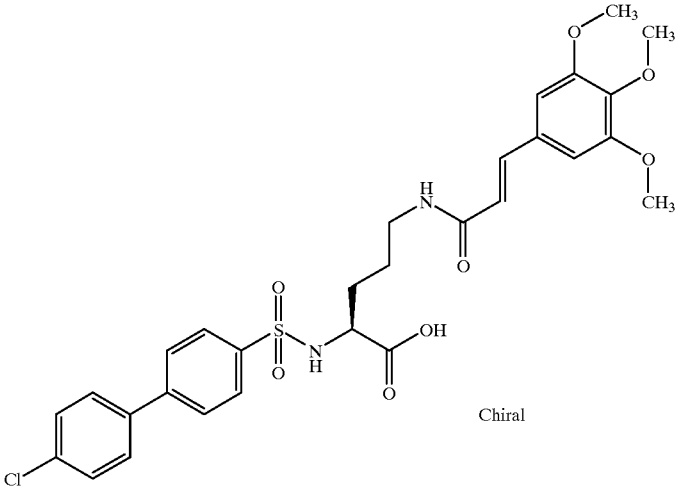 | | 603.2 | S |
| 125 | 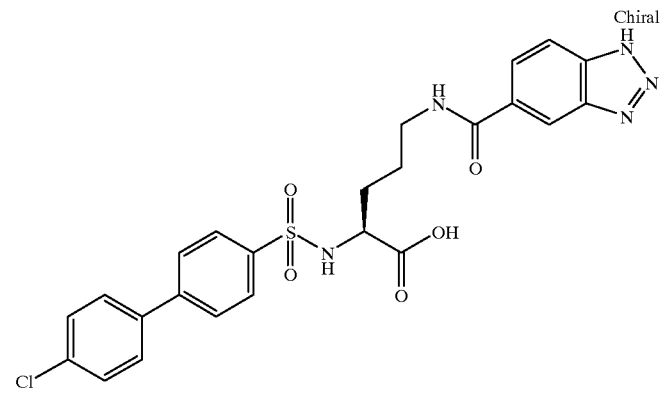 | | 528.2 | S |
| 126 | 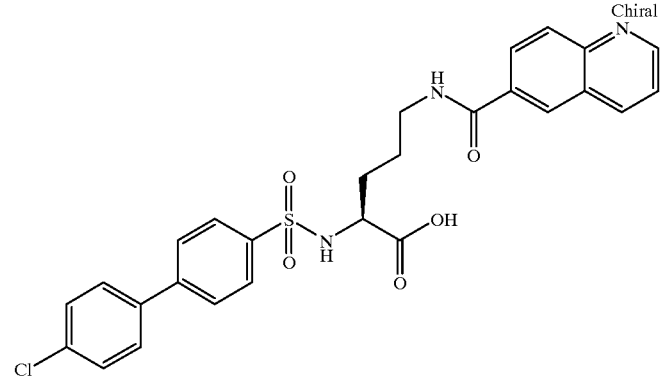 | | 538.2 | S |

TABLE 1-continued

| Ex. | Structure | M.P. (° C.) | MS (M + H) | Notes |
|---|---|---|---|---|
| 127 | 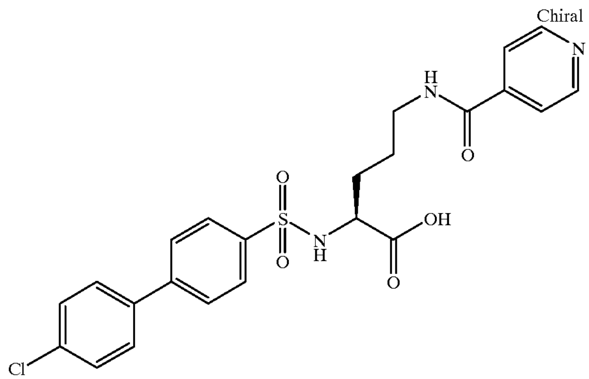 | | 488.2 | S |
| 128 | 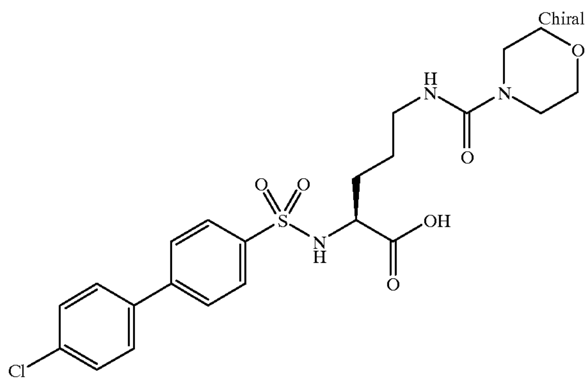 | | 496.2 | S |
| 129 | 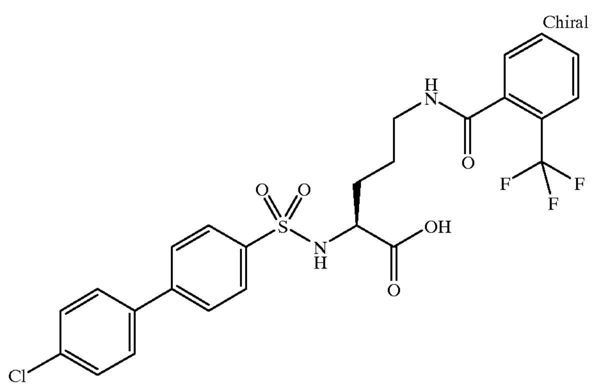 | | 555.2 | S |
| 130 | 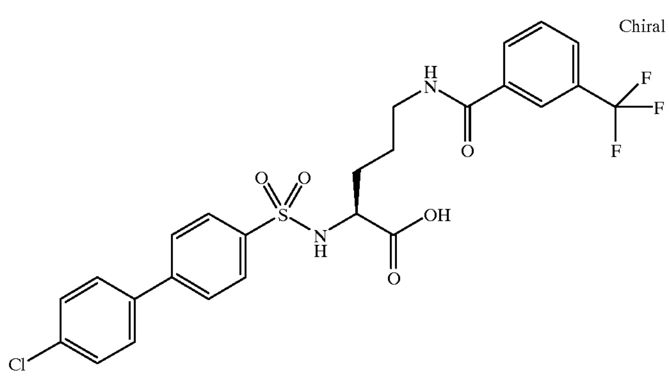 | | 555.2 | S |

6,159,995
TABLE 1-continued
| Ex. | Structure | M.P. (° C.) | MS (M + H) | Notes |
|---|---|---|---|---|
| 131 | 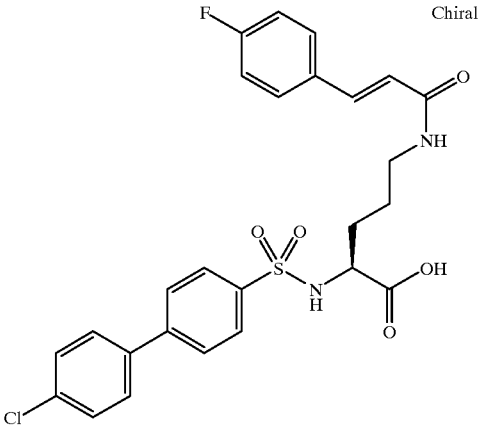 | | 531.2 | S |
| 132 | 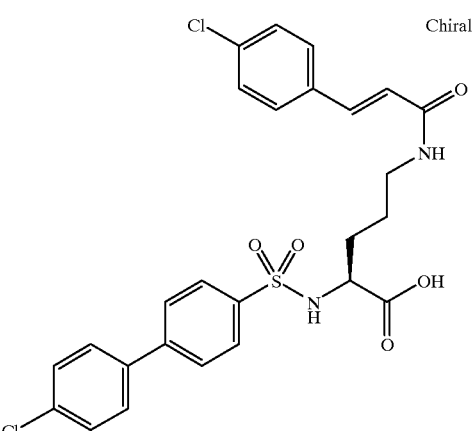 | | 547.2 | S |
| 133 | 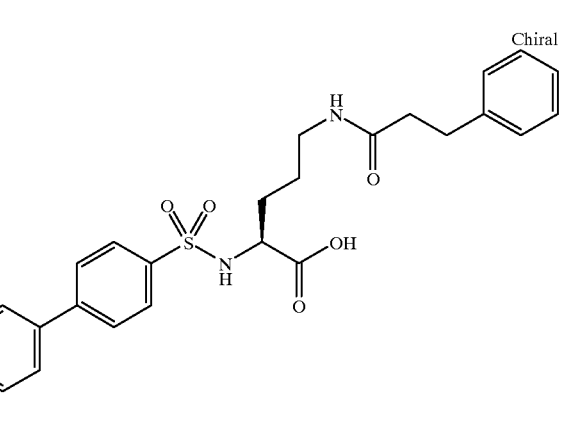 | | 515.3 | S |

TABLE 1-continued

| Ex. | Structure | M.P. (° C.) | MS (M + H) | Notes |
|-----|-----------|-------------|------------|-------|
| 134 | 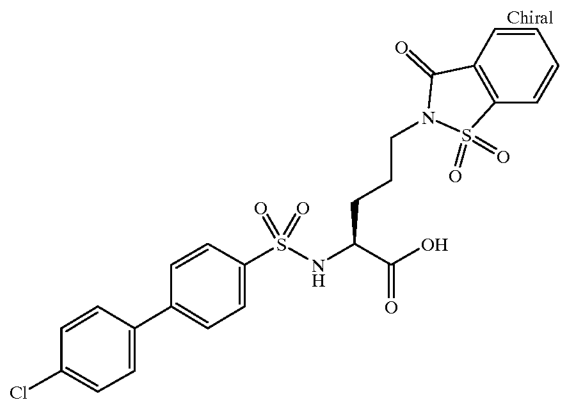 | | 549.1 | S |
| 135 | 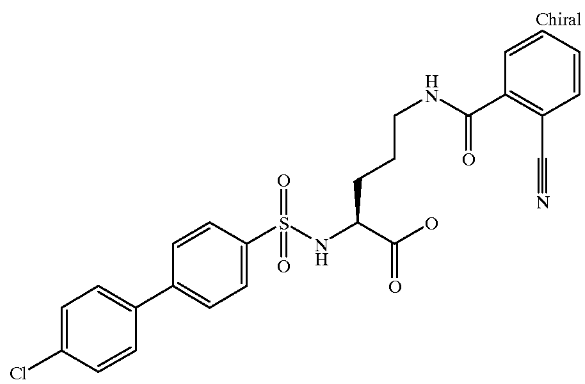 | | 512.2 | S |
| 136 | 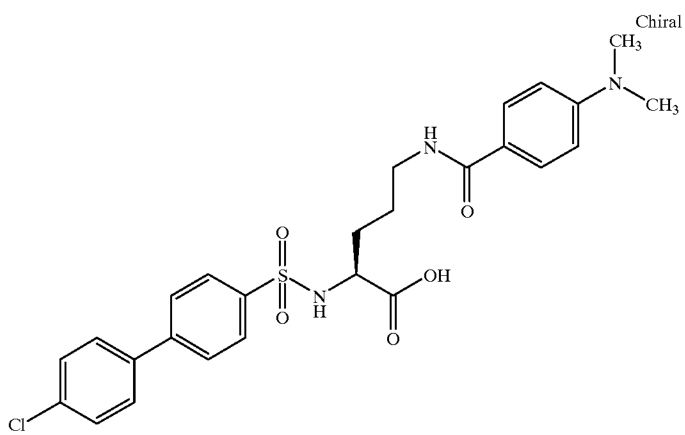 | | 530.2 | S |

TABLE 1-continued

| Ex. | Structure | M.P. (° C.) | MS (M + H) | Notes |
|---|---|---|---|---|
| 137 | 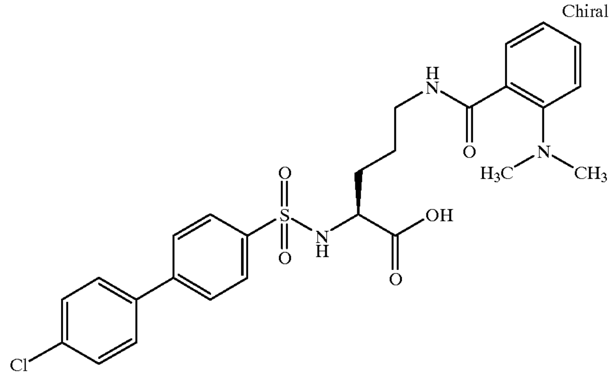 | | 530.2 | S |
| 138 | 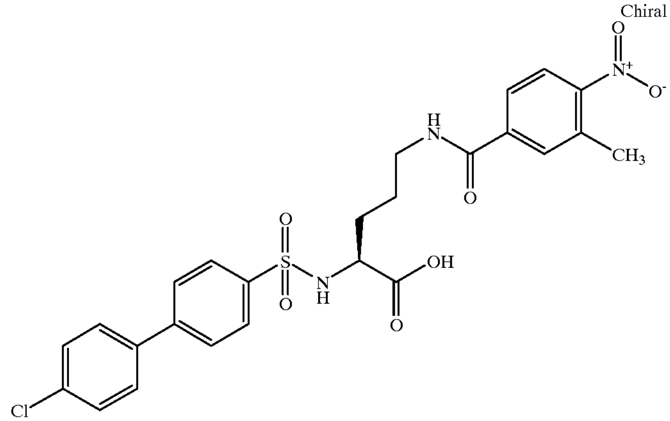 | | 546.2 | S |
| 139 | 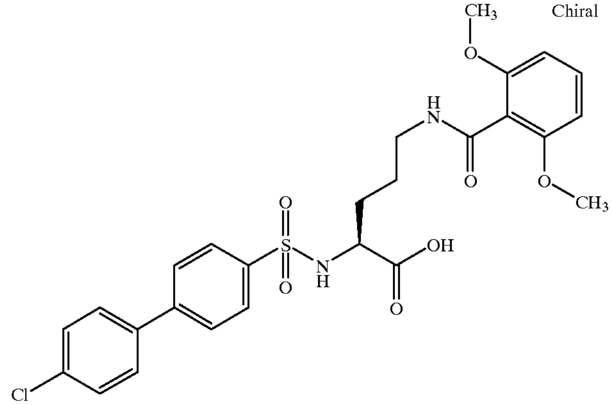 | | 547.2 | S |

TABLE 1-continued

| Ex. | Structure | M.P. (° C.) | MS (M + H) | Notes |
|---|---|---|---|---|
| 140 | 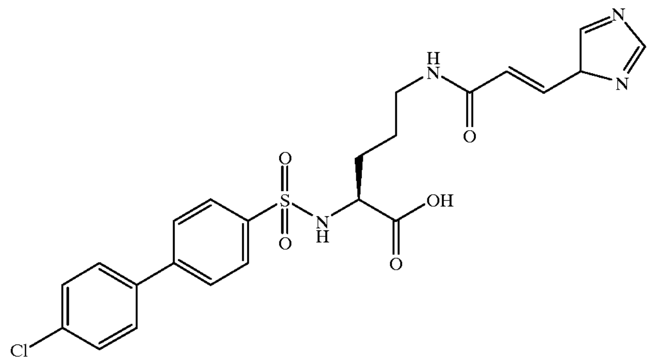 | | 503.2 | S |
| 141 | 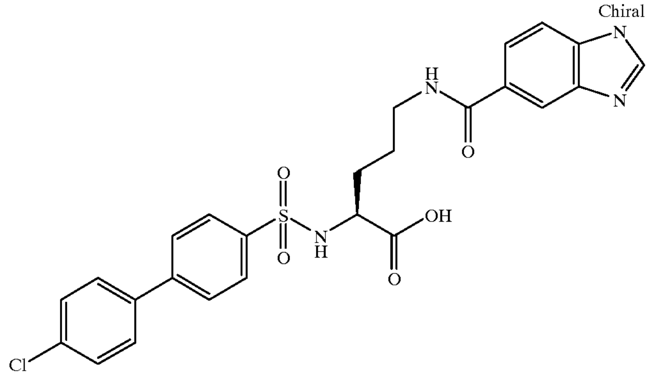 | | 527.2 | S |
| 142 | 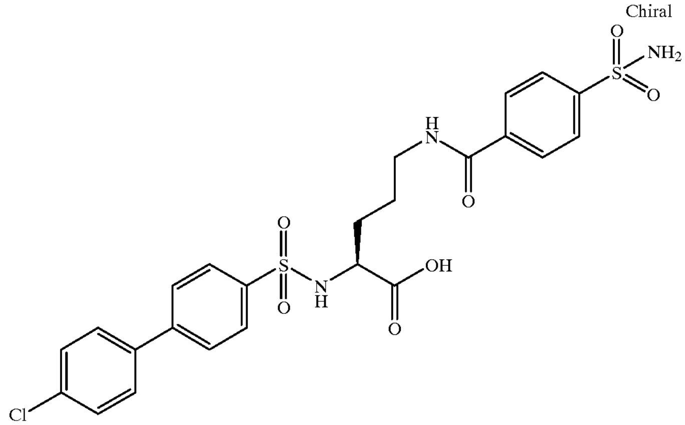 | | 566.2 | S |

TABLE 1-continued

| Ex. | Structure | M.P. (° C.) | MS (M + H) | Notes |
|---|---|---|---|---|
| 143 | 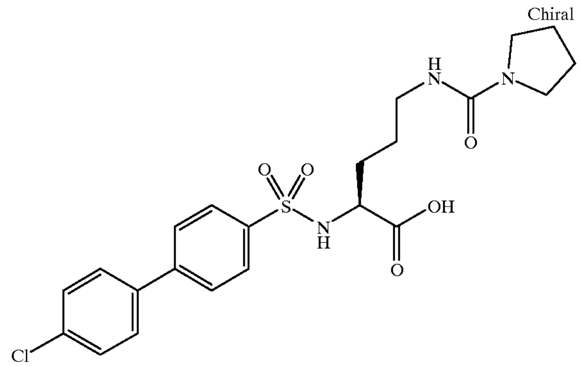 | | 480.2 | S |
| 144 | 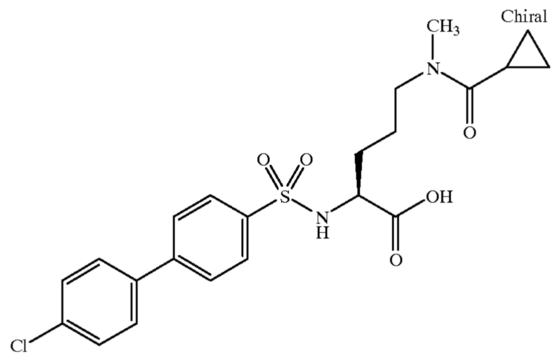 | | 465.3 | S |
| 145 | 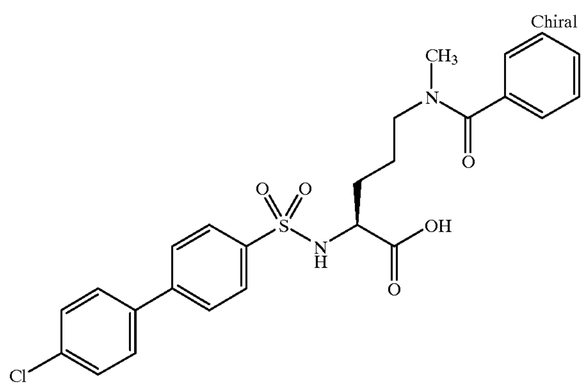 | | 487.3 | S |
| 146 | 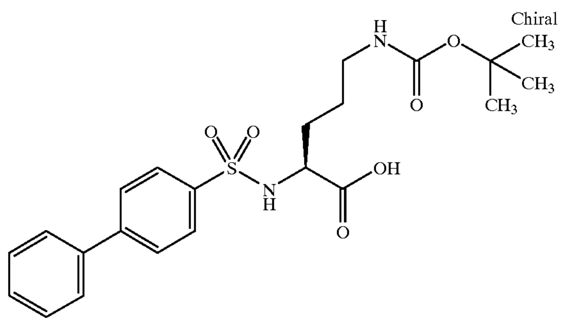 | | 449.2 | S |

| Ex. | Structure | M.P. (° C.) | MS (M + H) | Notes |
|---|---|---|---|---|
| 147 | 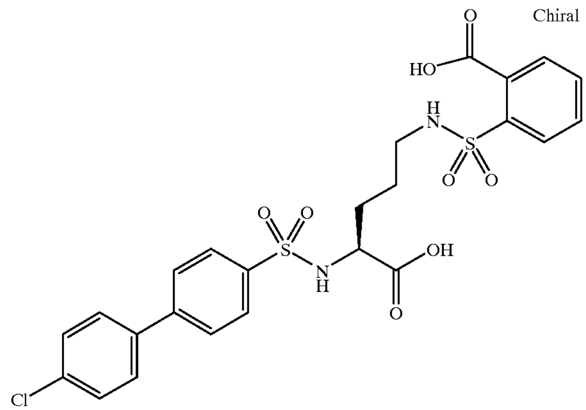 | | 458.2 | S,S |
| 148 | 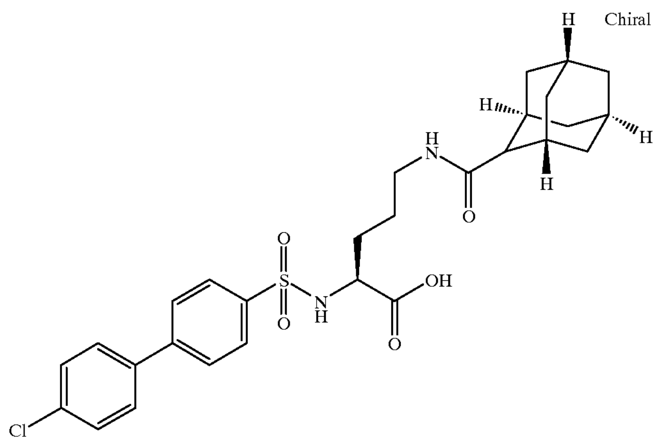 | | 545.3 | S |
| 149 | 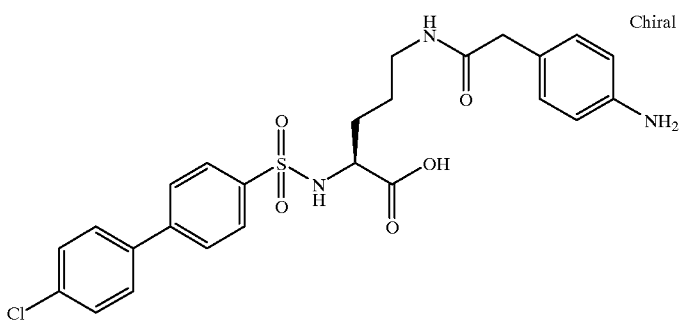 | | 516.2 | S |
| 150 | 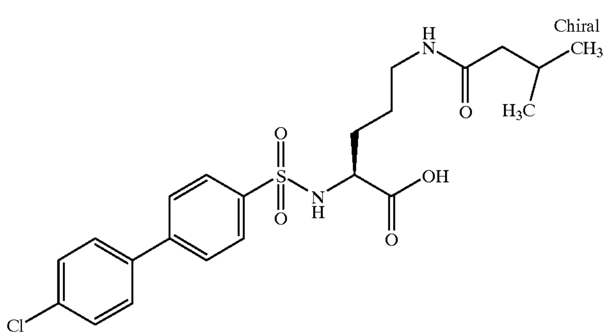 | | 467.2 | S |

TABLE 1-continued
| Ex. | Structure | M.P. (° C.) | MS (M + H) | Notes |
|---|---|---|---|---|
| 151 | 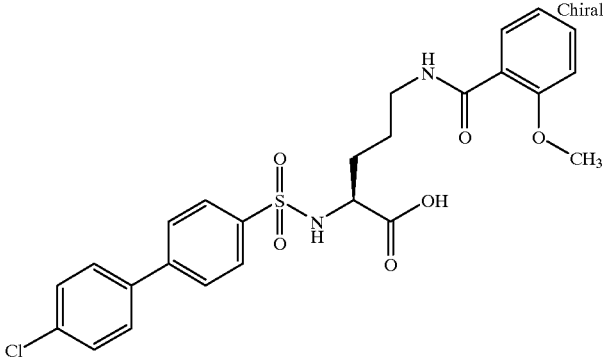 | | 517.2 | S |
| 152 | 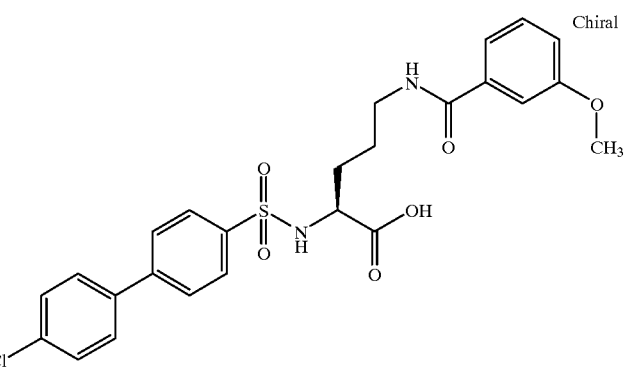 | | 517.2 | S |
| 153 | 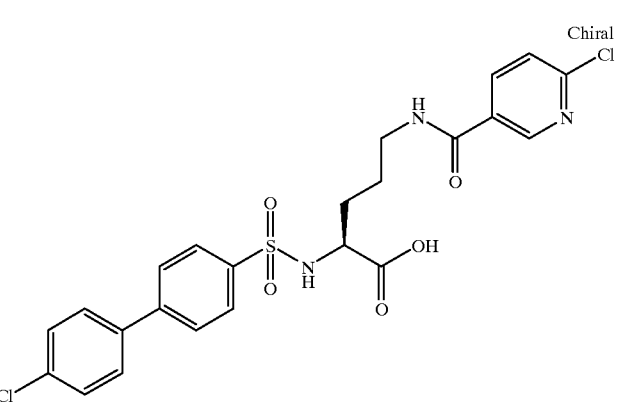 | | 522 | S |
| 154 | 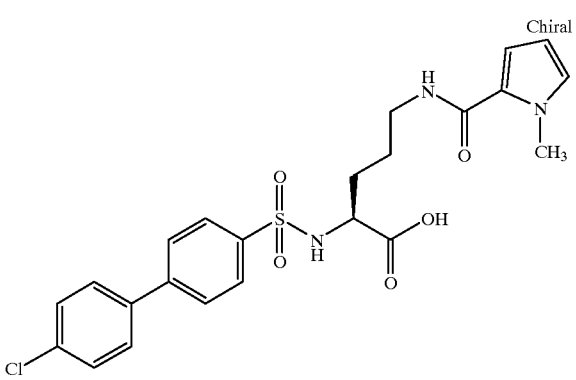 | | 490.2 | S |

TABLE 1-continued
| Ex. | Structure | M.P. (° C.) | MS (M + H) | Notes |
|---|---|---|---|---|
| 155 | 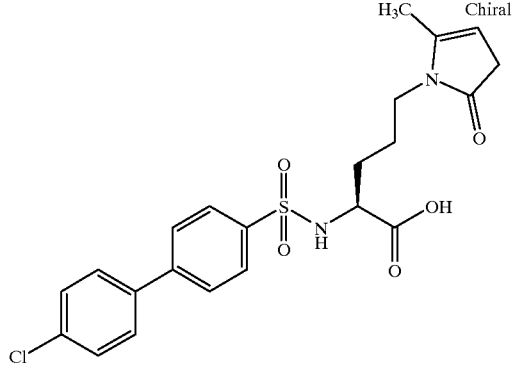 | | 463 | S |
| 156 | 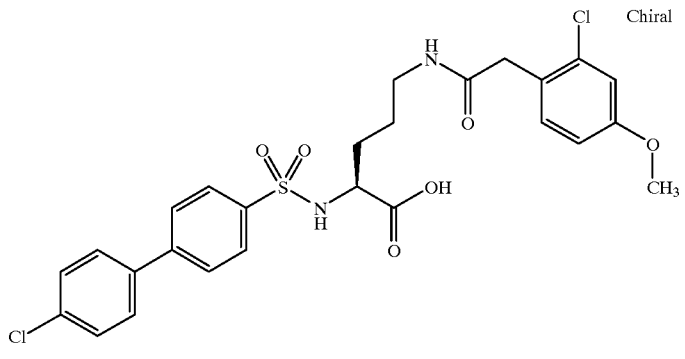 | | 551.2 | S |
| 157 | 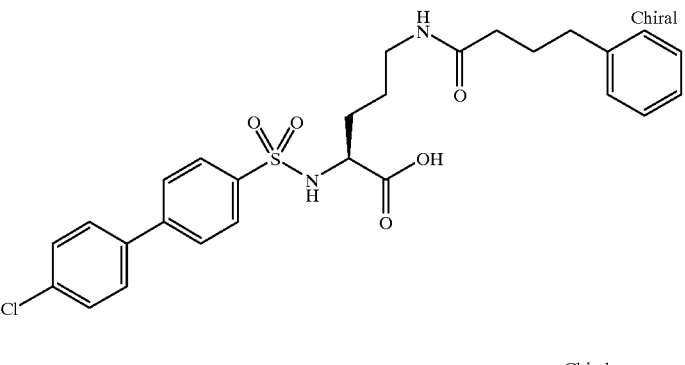 | | 529.2 | S |
| 158 | 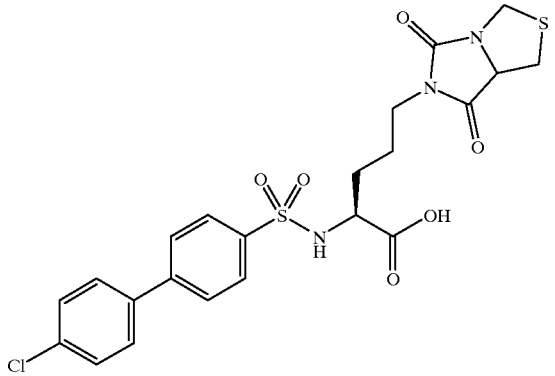 | | 524.0 | S |

TABLE 1-continued

| Ex. | Structure | M.P. (° C.) | MS (M + H) | Notes |
|---|---|---|---|---|
| 159 | 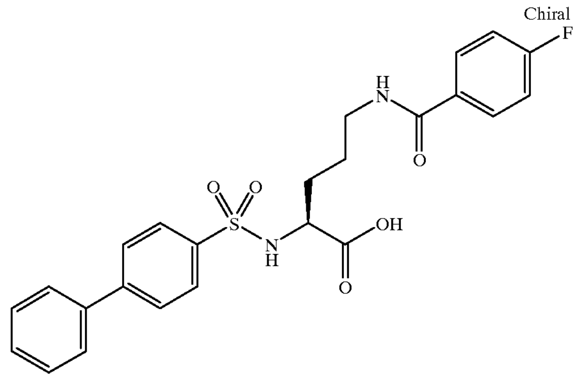 | | 471.2 | S |
| 160 | 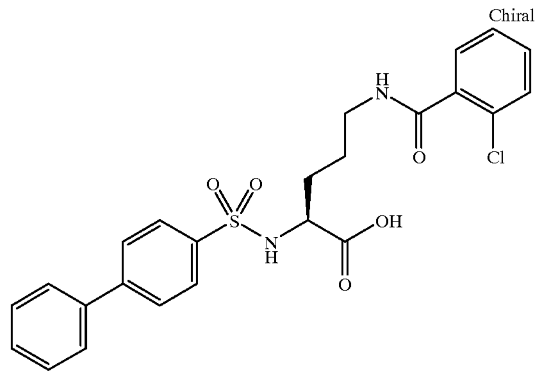 | | 487.1 | S |
| 161 | 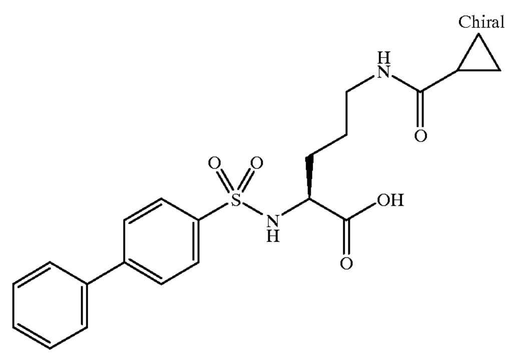 | | 417.2 | S |
| 162 | 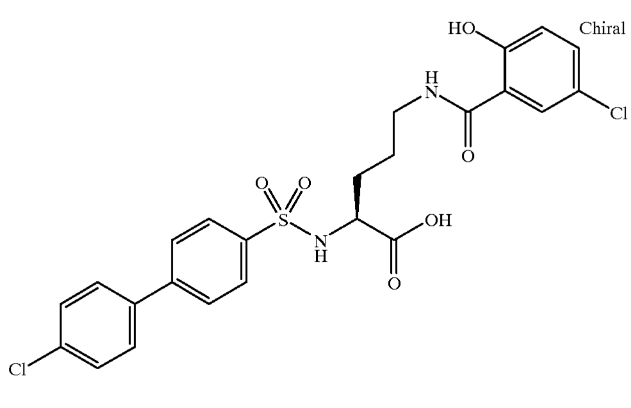 | | 537.1 | S |

TABLE 1-continued

| Ex. | Structure | M.P. (° C.) | MS (M + H) | Notes |
|---|---|---|---|---|
| 163 | 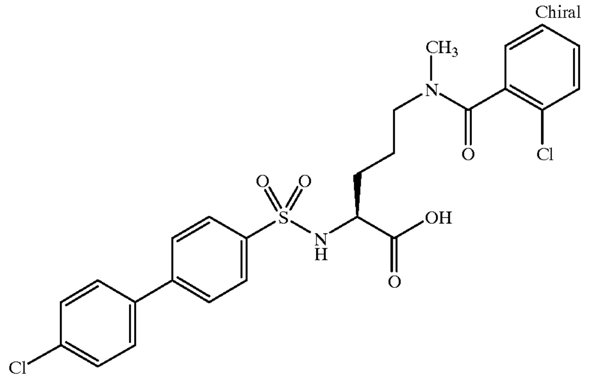 | | 535.1 | S |
| 164 | 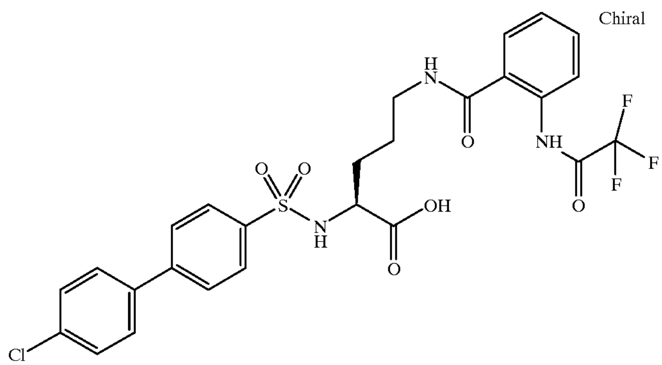 | | 598.1 | S |
| 165 | 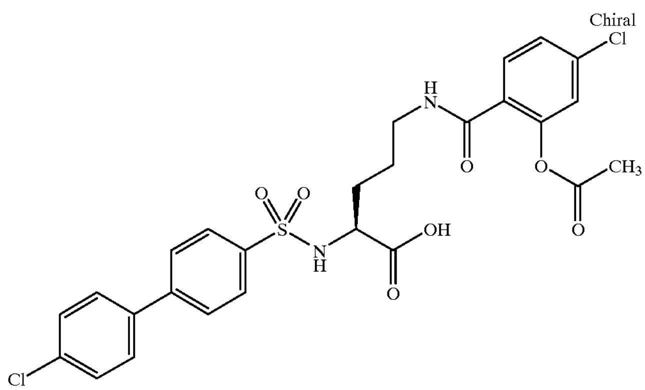 | | 579.2 | S |

TABLE 1-continued
| Ex. | Structure | M.P. (° C.) | MS (M + H) | Notes |
|---|---|---|---|---|
| 166 | 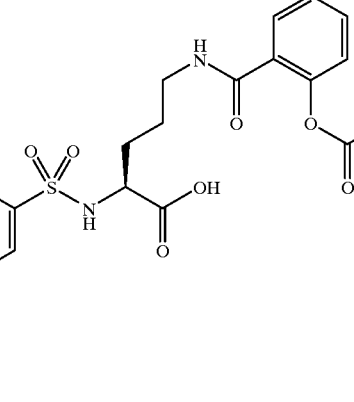 | | 579.2 | S |
| 167 | 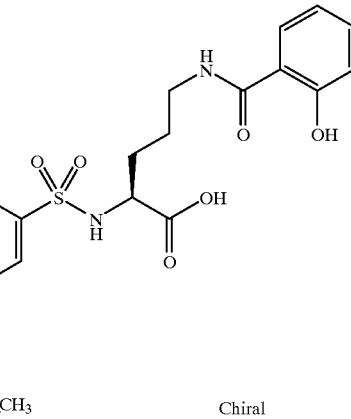 | | 537.2 | S |
| 168 | 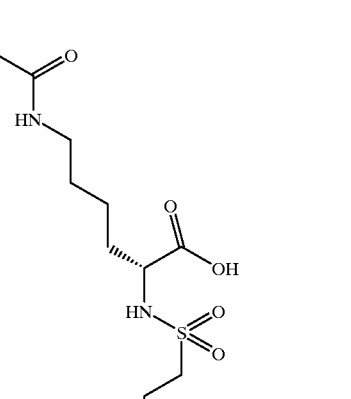 | | 500.2 | R |

TABLE 1-continued

| Ex. | Structure | M.P. (° C.) | MS (M + H) | Notes |
|---|---|---|---|---|
| 169 | 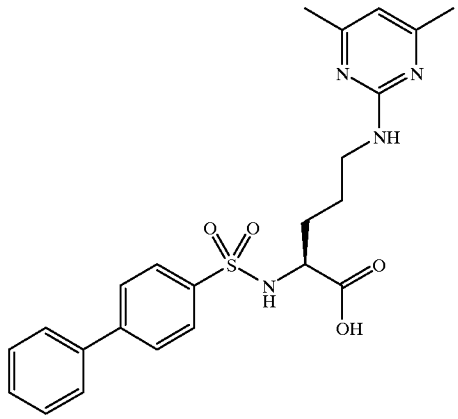 | 226–227° C. | | S |
| 170 | 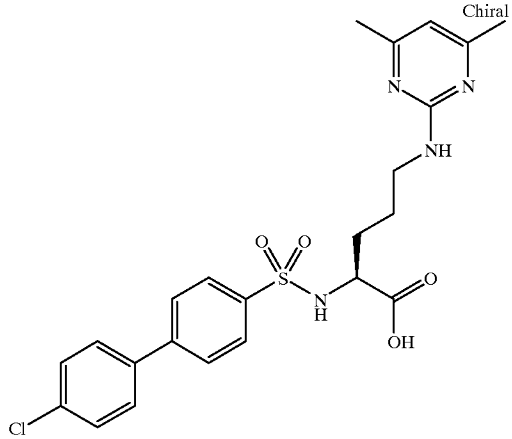 | 177–179° C. | | S |
| 171 | 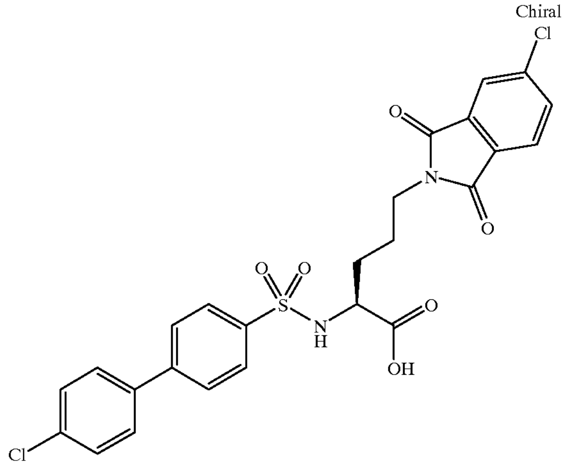 | | 547 | S |

TABLE 1-continued

| Ex. | Structure | | M.P. (° C.) | MS (M + H) | Notes |
|---|---|---|---|---|---|
| 172 | 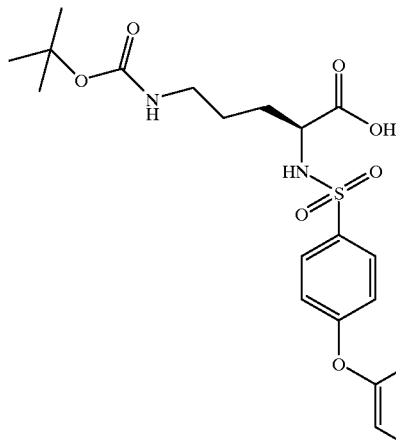 | Chiral | 131–133° C. | | |

Pharmacological Examples

Preparation and determination of the enzymatic activity of the catalytic domains of human stromelysin and of neutrophil collagenase.

The enzymes stromelysin (MMP-3) and neutrophil collagenase (MMP-8) were prepared according to Ye et al. (*Biochemistry*; 31 (1992) pages 11231–11235). To measure the enzyme activity or the enzyme inhibitor action, 70 µl of buffer solution and 10 µl of enzyme solution are incubated for 15 min with 10 µl of a 10% strength (v/v) aqueous dimethyl sulfoxide solution, which optionally contains the enzyme inhibitor. After addition of 10 µl of a 10% strength (v/v) aqueous dimethyl sulfoxide solution which contains 1 mil/L of the substrates, the enzyme reaction is monitored by fluorescence spectroscopy (328 nm (ex)/393 nm(em)). The enzyme activity is shown as the extinction increase/min. The IC50 values listed in Table 2 are determined as those inhibitor concentrations which in each case lead to a 50% inhibition of the enzyme.

The buffer solution contains 0.05% Brij (Sigma, Deisenhofen, Germany) and also 0.1 mol/L tris/HCl, 0.1 mol/L NaCl, 0.01 mol/L $CaCl_2$ and 0.1 mol/L piperazine-N,N'-bis(2-ethanesulfonic acid) (pH=6.5). The enzyme solution contains 5 µg/ml of one of the enzyme domains prepared according to Ye et al. The substrate solution contains 1 mil/L of the fluorogenic substrate (7-methoxycoumarin4-yl)acetyl-Pro-Leu-Gly-Leu-3-(2',4'-dinitrophenyl)-L-2,3-diaminopropionyl-Ala-Arg-$NH_2$ (Bachem, Heidelberg, Germany).

TABLE 2

| Example | IC50 MMP-3 [× $10^{-9}$ mol/L] | IC50 MMP-8 [× $10^{-9}$ mol/l] |
|---|---|---|
| 1 | 50 | 7 |
| 2 | 20 | 6 |
| 4 | 90 | 20 |
| 5 | 50 | 4 |
| 6 | 5 | 2 |
| 7 | 4 | 2 |
| 9 | 60 | 70 |

TABLE 2-continued

| Example | IC50 MMP-3 [× $10^{-9}$ mol/L] | IC50 MMP-8 [× $10^{-9}$ mol/l] |
|---|---|---|
| 12 | 60 | 10 |
| 14 | 5 | 3 |
| 15 | 20 | 8 |
| 16 | 20 | 10 |
| 18 | 70 | 10 |
| 19 | 20 | 5 |
| 20 | 40 | 7 |
| 21 | 70 | 20 |
| 22 | 80 | 80 |
| 23 | 40 | 5 |
| 24 | 30 | 5 |
| 25 | 60 | 10 |
| 26 | 60 | 7 |
| 28 | 40 | 6 |
| 29 | 6 | 3 |
| 30 | 30 | 5 |
| 31 | 5 | 2 |
| 32 | 6 | 2 |
| 34 | 4 | 2 |
| 36 | 5 | 2 |
| 38 | 5 | 2 |
| 39 | 20 | 30 |
| 41 | 5 | 2 |
| 42 | 10 | 3 |
| 43 | 40 | 20 |
| 44 | 30 | 6 |
| 45 | 20 | 4 |
| 46 | 10 | 3 |
| 47 | 10 | 3 |
| 48 | 20 | 7 |
| 49 | 20 | 3 |
| 50 | 6 | 2 |
| 51 | 20 | 3 |
| 52 | 20 | 10 |
| 53 | 30 | 6 |
| 55 | 7 | 3 |
| 56 | 10 | 8 |
| 57 | 40 | 8 |
| 59 | 5 | 1 |
| 60 | 10 | 10 |
| 61 | 6 | 2 |
| 62 | 5 | 2 |
| 63 | 10 | 2 |

TABLE 2-continued

| Example | IC50 MMP-3 [× 10⁻⁹ mol/L] | IC50 MMP-8 [× 10⁻⁹ mol/l] |
|---|---|---|
| 64 | 30 | 2 |
| 65 | 20 | 4 |
| 66 | 10 | 2 |
| 69 | 4 | 2 |
| 70 | 10 | 3 |
| 71 | 10 | 3 |
| 72 | 20 | 6 |
| 73 | 4 | 2 |
| 74 | 10 | 3 |
| 75 | 20 | 4 |
| 76 | 40 | 40 |
| 77 | 10 | 2 |
| 79 | 5 | 2 |
| 80 | 10 | 3 |
| 81 | 30 | 3 |
| 82 | 20 | 4 |
| 83 | 7 | 3 |
| 84 | 20 | 4 |
| 85 | 20 | 5 |
| 86 | 20 | 4 |
| 87 | 30 | 10 |
| 88 | 10 | 3 |
| 89 | 30 | 10 |
| 90 | 20 | 5 |
| 91 | 30 | 5 |
| 92 | 40 | 20 |
| 93 | 20 | 4 |
| 94 | 30 | 5 |
| 95 | 20 | 4 |
| 96 | 20 | 6 |
| 97 | 20 | 4 |
| 98 | 10 | 3 |
| 99 | 5 | 2 |
| 100 | 4 | 2 |
| 101 | 40 | 10 |
| 102 | 20 | 5 |
| 103 | 70 | 60 |
| 104 | 30 | 8 |
| 105 | 40 | 10 |
| 106 | 60 | 30 |
| 107 | 10 | 4 |
| 108 | 20 | 5 |
| 109 | 20 | 7 |
| 110 | 40 | 20 |
| 111 | 10 | 3 |
| 113 | 5 | 3 |
| 114 | 5 | 2 |
| 115 | 5 | 3 |
| 116 | 20 | 4 |
| 117 | 9 | 2 |
| 118 | 10 | 4 |
| 120 | 20 | 4 |
| 122 | 3 | 2 |
| 123 | 60 | 10 |
| 125 | 10 | 10 |
| 126 | 30 | 10 |
| 127 | 20 | 3 |
| 128 | 5 | 2 |
| 129 | 10 | 2 |
| 130 | 20 | 4 |
| 131 | 20 | 5 |
| 132 | 30 | 10 |
| 133 | 5 | 2 |
| 134 | 5 | 2 |
| 135 | 30 | 8 |
| 136 | 10 | 7 |
| 137 | 20 | 7 |
| 138 | 30 | 10 |
| 139 | 50 | 20 |
| 140 | 60 | 20 |
| 141 | 10 | 10 |
| 142 | 10 | 4 |
| 143 | 5 | 2 |
| 144 | 10 | 3 |
| 145 | 10 | 5 |
| 146 | 30 | 3 |

TABLE 2-continued

| Example | IC50 MMP-3 [× 10⁻⁹ mol/L] | IC50 MMP-8 [× 10⁻⁹ mol/l] |
|---|---|---|
| 151 | 30 | 10 |
| 152 | 60 | 10 |
| 154 | 30 | 9 |
| 155 | 50 | 10 |
| 156 | 60 | 20 |
| 157 | 40 | 7 |
| 158 | 7 | 2 |
| 160 | 70 | 10 |
| 161 | 40 | 4 |
| 162 | 50 | 6 |
| 168 | 40 | 20 |
| 170 | 20 | 10 |
| 171 | 30 | 10 |

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

We claim:

1. A compound of formula (I) in any of its stereoisomeric forms:

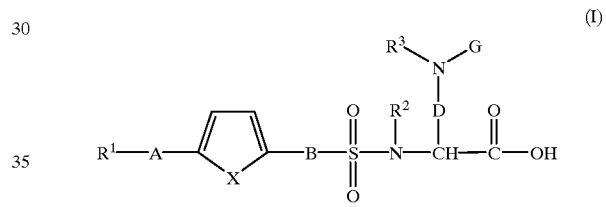

a physiologically tolerable salt thereof, or a mixture of any of the foregoing, wherein $R^1$ is (A) unsubstituted phenyl, (B) phenyl, which is mono- or disubstituted by at least one radical, which in the case of a disubstituted phenyl are the same or different radicals, selected from (B)(1) $(C_1-C_7)$-alkyl-, (B)(2) —OH.

(B)(3) $(C_1-C_6)$-alkyl-C(O)—O—.

(B)(4) $(C_1-C_6)$-alkyl-O—, (B)(5) $(C_1-C_6)$-alkyl-O—$(C_1-C_4)$-alkyl-O—.

(B)(6) halogen, (B)(7) —$CF_3$, (B)(8) —CN, (B)(9) —$NO_2$, (B)(10) HO—C(O)—, (B)(11) $(C_1-C_6)$-alkyl-O—C(O)—, (B)(12) methylenedioxo, (B)(13) $R^4$—$(R^5)$N—C(O)—, and (B)(14) $R^4$—$(R^5)$N—, or (C) a heteroaromatic ring structure, as defined under (C)(1) to (C)(16) below, wherein the heteroaromatic ring structure is unsubstituted, or substituted by at least one radical selected from (B)(1) to (B)(14) above, wherein the heteroaromatic ring structure is selected from (C)(1) pyrrole, (C)(2) pyrazole, (C)(3) imidazole,
(C)(4) triazole,
(C)(5) thiophene,
(C)(6) thiazole,
(C)(7) oxazole,
(C)(8) isoxazole,
(C)(9) pyridine,
(C)(10) pyrimidine,
(C)(11) indole,
(C)(12) benzothiophene,
(C)(13) benzimidazole,
(C)(14) benzoxazole,
(C)(1 5) benzothiazole, and
(C)(16) benzotriazole;

$R^2$, $R^4$, and $R^5$ are the same or different, and each is independently selected from
(1) a hydrogen atom,
(2) ($C_1$–$C_6$)-alkyl-,
(3) HO—C(O)—($C_1$–$C_6$)-alkyl-,
(4) phenyl-$(CH_2)_a$—, wherein phenyl is unsubstituted, or mono- or disubstituted by at least one radical which in the case of a disubstituted phenyl are the same or different radicals, selected from (B)(1) to (B)(14) above, and wherein a is the integer zero, 1, or 2,
(5) picolyl, and
(6) $R^4$ and $R^5$ together with the ring amino group form a 4- to 7-membered ring, wherein one of the carbonyl atoms is optionally replaced by —O—, —S—, or —NH—;

$R^3$ and G are bonded to a nitrogen atom to form a five-membered heteroatom ring selected from the following subformulae:

(IIa)

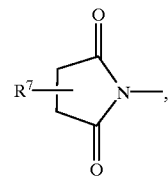

(IIb)

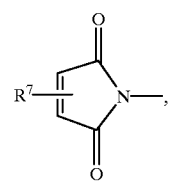

(IIc)

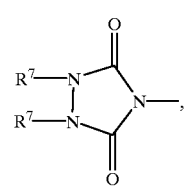

(IId)

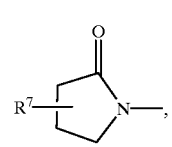

-continued (IIe)

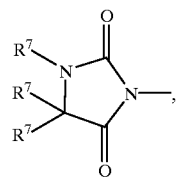

(IIf)

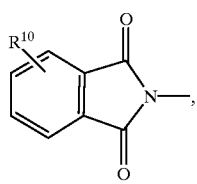

(IIg)

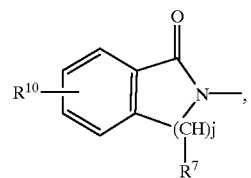

(IIh)

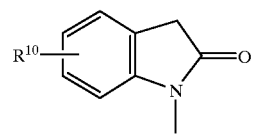

(IIi)

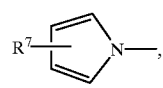

(IIj)

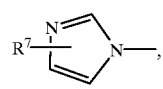

(IIk)

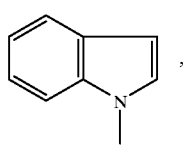

(IIl)

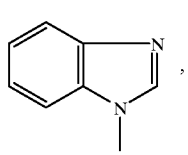

-continued

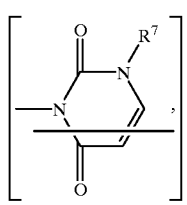
(IIm)

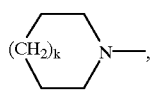
(IIn)

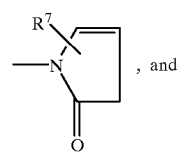
(IIo), and

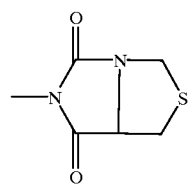
(IIp)

wherein j is the integer 1, $R^{10}$ is at least one radical selected from (B)(1) to (B)(14) above, $R^7$ is a hydrogen atom, or ($C_1$–$C_6$-alkyl, and k is zero;

A is
(a) a covalent bond,
(b) —O—,
(c) —CH=CH—, or
(d) —C≡C—;

B is
(a) —(CH$_2$)$_l$— wherein 1 is the integer zero, 1, 2, or 3,
(b) —O—(CH$_2$)$_m$— wherein m is the integer 1, 2, 3, 4, or 5, or
(c) —CH=CH—;

D is —(CH$_2$)$_n$—, wherein n is the integer 1, 2, 3, 4, 5, or 6, and wherein at least one of the —(CH$_2$)$_n$— carbon atoms is optionally replaced by an optionally substituted —N—, —O—, or —S— atom; and X is —CH=CH—, an oxygen atom, or a sulfur atom.

2. A pharmaceutical composition comprising at least one compound of claim 1, and a pharmaceutically suitable or physiologically tolerable excipient.

3. A method of treating a disorder comprising the step of administering to a host in need thereof an amount of at least one compound of claim 1, which is efficacious in the treatment of a degenerative joint disorder; osteoarthroses, spondyloses, or chondrolysis, any of which resulting from joint trauma or relatively long immobilization of the joint or resulting from meniscus or patella injuries or tears of the ligaments.

4. A method of treating a disorder comprising the step of administering to a host in need thereof an amount of at least one compound of claim 1 which is efficacious in the treatment of connective tissue, periodontal, or wound healing disorders or in the treatment of collagenoses.

5. A method of treating a disorder comprising the step of administering to a host in need thereof an amount of at least one compound of claim 1 wherein the disorder is a chronic disorder of the locomotory apparatus, or in the treatment of inflammatory, immunologically or metabolically related acute or chronic arthritides, arthropathies, or myalgias.

6. A method of treating a disorder, comprising the step of administering to a host in need thereof an amount of at least one compound of claim 1 which is efficacious in the treatment of a disorder of bone metabolism, ulceration, atherosclerosis, stenoses, inflammation, carcinomatous disorders, formation of tumor metastases, cachexia, anorexia, or septic shock.

7. A compound of formula (I) in any of its stereoisomeric forms:

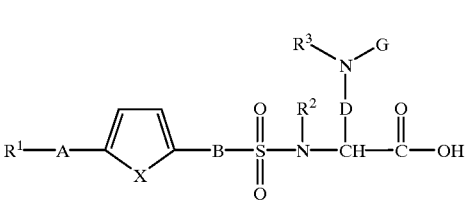
(I)

a physiologically tolerable salt thereof, or a mixture of any of the foregoing, wherein $R_1$ is
(A) unsubstituted phenyl, or
(B) phenyl, which is monosubstituted by at least one radical selected from
  (B)(1a) halogen, and
  (B)(2) $R^4$—($R^5$)N— wherein $R^4$ and $R^5$ are the same or different and each is selected from
    (B)(2)(a) ($C_1$–$C_3$)-alkyl-, and
    (B)(2)(b) $R^4$ and $R^5$ together with the ring amino group form a 5- to 6-membered ring wherein at least one of the carbon atoms is optionally replaced by —O— or —NH—;

$R^2$ is a hydrogen atom;

$R^3$ and G are bonded by a nitrogen atom to form a ring of the following subformula

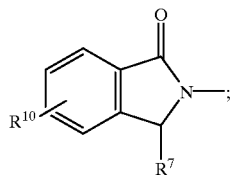

$R^7$ is a hydrogen atom or ($C_1$–$C_6$) alkyl.

$R^{10}$ is selected from
(B)(1) ($C_1$–$C_7$)-alkyl-,
(B)(2) —OH,
(B)(3) ($C_1$–$C_6$)-alkyl-C(O)—O—,
(B)(4) ($C_1$–$C_6$)-alkyl-O—,
(B)(5) ($C_1$–$C_6$)-alkyl-O—($C_1$–$C_4$)-alkyl-O—,
(B)(6) halogen,
(B)(7) —CF$_3$,
(B)(8) —CN,
(B)(9) —NO$_2$,
(B)(10) HO—C(O)—,
(B)(11) ($C_1$–$C_6$)-alkyl-O—C(O)—,
(B)(12) methylenedioxo,
(B)(13) $R^4$—($R^5$)N—C(O)—, and
(B)(14) $R^4$—($R^5$)N—, A is a covalent bond;

B is —(CH$_2$)$_q$— wherein q is zero;

D is —(CH$_2$)$_r$— wherein r is the integer 2, 3, or 4; and

X is —CH=CH—.

8. A compound of claim 7, wherein the halogen radical (B)(1a) is chlorine or fluorine.

9. A pharmaceutical composition comprising at least one compound of claim 7 and a pharmaceutically suitable or physiologically tolerable excipient.

10. A method of treating a disorder comprising the step of administering to a host in need thereof an amount of at least one compound of claim 7 which is efficacious in the treatment of a degenerative joint disorder; osteoarthroses, spondyloses, or chondrolysis, any of which resulting from joint trauma or relatively long immobilization of the joint, or resulting from meniscus or patella injuries or tears of the ligaments.

11. A method of treating a disorder comprising the step of administering to a host in need thereof an amount of at least one compound of claim 7 which is efficacious in the treatment of connective tissue, periodontal, or wound healing disorders, or in the treatment of collagenoses.

12. A method of treating a disorder comprising the step of administering to a host in need thereof an amount of at least one compound of claim 7 which is efficacious in the treatment of a chronic disorder of the locomotory apparatus; or in the treatment of inflammatory, immunologically or metabolically related acute or chronic arthritides, arthropathies, or myalgias.

13. A method of treating a disorder comprising the step of administering to a host in need thereof an amount of at least one compound of claim 7 which is efficacious in the treatment of a disorder of bone metabolism, ulceration, atherosclerosis, stenoses, inflammation, carcinomatous disorders, formation of tumor metastases, cachexia, anorexia, or septic shock.

* * * * *